(12) United States Patent
Park

(10) Patent No.: US 8,460,303 B2
(45) Date of Patent: Jun. 11, 2013

(54) ARTHROPLASTY SYSTEMS AND DEVICES, AND RELATED METHODS

(75) Inventor: Ilwhan Park, Walnut Creek, CA (US)

(73) Assignee: OtisMed Corporation, Alameda, CA (US)

( * ) Notice: Subject to any disclaimer, the term of this patent is extended or adjusted under 35 U.S.C. 154(b) by 1440 days.

(21) Appl. No.: 11/924,425

(22) Filed: Oct. 25, 2007

(65) Prior Publication Data

US 2009/0110498 A1    Apr. 30, 2009

(51) Int. Cl.
*A61F 5/00*  (2006.01)
(52) U.S. Cl.
USPC ............... 606/87; 606/86 R; 606/89; 409/219
(58) Field of Classification Search
USPC ................ 606/86 R–89, 293; 409/2, 3, 79, 409/80, 282, 291, 292, 903, 6, 7, 175, 219, 409/224, 227
See application file for complete search history.

(56) References Cited

U.S. PATENT DOCUMENTS

| | | |
|---|---|---|
| 3,195,411 A | 7/1965 | MacDonald et al. |
| 3,825,151 A | 7/1974 | Arnaud |
| D245,920 S | 9/1977 | Shen |
| 4,198,712 A | 4/1980 | Swanson |
| 4,298,992 A | 11/1981 | Burstein |
| 4,436,684 A | 3/1984 | White |
| D274,093 S | 5/1984 | Kenna |
| D274,161 S | 6/1984 | Kenna |
| 4,467,801 A | 8/1984 | Whiteside |
| 4,575,330 A | 3/1986 | Hull |
| 4,646,726 A | 3/1987 | Westin et al. |
| 4,719,585 A | 1/1988 | Cline et al. |
| 4,721,104 A | 1/1988 | Kaufman et al. |
| 4,821,213 A | 4/1989 | Cline et al. |
| 4,822,365 A | 4/1989 | Walker et al. |
| 4,825,857 A | 5/1989 | Kenna |
| 4,841,975 A | 6/1989 | Woolson |
| 4,931,056 A | 6/1990 | Ghajar et al. |
| 4,936,862 A | 6/1990 | Walker et al. |

(Continued)

FOREIGN PATENT DOCUMENTS

| | | |
|---|---|---|
| DE | 3305237 | 2/1983 |
| DE | 4341367 C1 | 6/1995 |

(Continued)

OTHER PUBLICATIONS

Eisenhart-Rothe et al., "Femorotibial and Patellar Cartilage Loss in Patients Prior to Total Knee arthroplasty, Heterogeneity, and Correlation with alignment of the Knee," Ann Rheum Dis., Jun. 2005 (BMJ Publishing Group Ltd & European League Against Rheumatism).

(Continued)

*Primary Examiner* — Andrew Yang
(74) *Attorney, Agent, or Firm* — Polsinelli PC

(57) ABSTRACT

Systems for manufacturing arthroplasty jigs are disclosed. The systems include positioning components for positioning an arthroplasty jig blank in a machining device (e.g., a computer numerical control (CNC) machine). Arthroplasty jig blanks that may be used in the systems can include an arm fixture component configured to be coupled to the positioning component. Coupling the arm fixture component to the positioning component positions the jig blank body for machining by the machining device. In addition, positioning components, arthroplasty jig blanks, and methods for making arthroplasty jig blanks are disclosed.

21 Claims, 18 Drawing Sheets

U.S. PATENT DOCUMENTS

| | | |
|---|---|---|
| 4,976,737 A | 12/1990 | Leake |
| 5,007,936 A | 4/1991 | Woolson |
| 5,011,405 A | 4/1991 | Lemchen |
| 5,027,281 A | 6/1991 | Rekow et al. |
| 5,030,219 A | 7/1991 | Matsen, III et al. |
| 5,037,424 A | 8/1991 | Aboczsky |
| 5,075,866 A | 12/1991 | Goto et al. |
| 5,078,719 A | 1/1992 | Schreiber |
| 5,086,401 A | 2/1992 | Glassman et al. |
| 5,098,383 A | 3/1992 | Hemmy et al. |
| 5,099,846 A | 3/1992 | Hardy |
| 5,122,144 A | 6/1992 | Bert et al. |
| 5,123,927 A | 6/1992 | Duncan et al. |
| 5,139,419 A | 8/1992 | Andreiko et al. |
| 5,140,646 A | 8/1992 | Ueda |
| 5,141,512 A | 8/1992 | Farmer et al. |
| 5,154,717 A | 10/1992 | Matsen, III et al. |
| 5,156,777 A | 10/1992 | Kaye |
| 5,171,276 A | 12/1992 | Caspari et al. |
| D336,518 S | 6/1993 | Taylor |
| 5,218,427 A | 6/1993 | Koch |
| 5,234,433 A | 8/1993 | Bert et al. |
| 5,236,461 A | 8/1993 | Forte |
| 5,274,565 A | 12/1993 | Reuben |
| 5,298,115 A | 3/1994 | Leonard |
| 5,305,203 A | 4/1994 | Raab |
| D346,979 S | 5/1994 | Stalcup et al. |
| 5,320,529 A | 6/1994 | Pompa |
| 5,360,446 A | 11/1994 | Kennedy |
| 5,364,402 A | 11/1994 | Mumme et al. |
| 5,365,996 A | 11/1994 | Crook |
| 5,368,478 A | 11/1994 | Andreiko et al. |
| D355,254 S | 2/1995 | Krafft et al. |
| D357,315 S | 4/1995 | Dietz |
| 5,408,409 A | 4/1995 | Glassman et al. |
| 5,431,562 A | 7/1995 | Andreiko et al. |
| 5,448,489 A | 9/1995 | Reuben |
| 5,452,407 A | 9/1995 | Crook |
| 5,462,550 A | 10/1995 | Dietz et al. |
| 5,484,446 A | 1/1996 | Burke et al. |
| D372,309 S | 7/1996 | Heldreth |
| D374,078 S | 9/1996 | Johnson et al. |
| 5,556,278 A | 9/1996 | Meitner |
| 5,569,260 A | 10/1996 | Petersen |
| 5,569,261 A | 10/1996 | Marik et al. |
| 5,601,563 A | 2/1997 | Burke et al. |
| 5,601,565 A | 2/1997 | Huebner |
| 5,662,656 A | 9/1997 | White |
| 5,681,354 A | 10/1997 | Eckhoff |
| 5,682,886 A | 11/1997 | Delp et al. |
| 5,683,398 A | 11/1997 | Carls et al. |
| 5,690,635 A | 11/1997 | Matsen, III et al. |
| 5,716,361 A | 2/1998 | Masini |
| 5,725,376 A | 3/1998 | Poirier |
| 5,735,277 A | 4/1998 | Schuster |
| 5,741,215 A | 4/1998 | D'Urso |
| 5,749,876 A | 5/1998 | Duvillier et al. |
| 5,768,134 A | 6/1998 | Swaelens |
| 5,769,092 A | 6/1998 | Williamson, Jr. |
| 5,769,859 A | 6/1998 | Dorsey |
| D398,058 S | 9/1998 | Collier |
| 5,810,830 A | 9/1998 | Noble et al. |
| 5,824,085 A | 10/1998 | Sahay et al. |
| 5,824,098 A | 10/1998 | Stein |
| 5,824,100 A | 10/1998 | Kester et al. |
| 5,824,111 A | 10/1998 | Schall et al. |
| 5,860,980 A | 1/1999 | Axelson, Jr. et al. |
| 5,860,981 A | 1/1999 | Bertin et al. |
| 5,871,018 A | 2/1999 | Delp et al. |
| 5,880,976 A | 3/1999 | DiGioia III et al. |
| 5,908,424 A | 6/1999 | Bertin et al. |
| 5,911,724 A | 6/1999 | Wehrli |
| 5,964,808 A | 10/1999 | Blaha et al. |
| 5,967,777 A | 10/1999 | Klein et al. |
| 5,993,448 A | 11/1999 | Remmler |
| 5,995,738 A | 11/1999 | DiGioia, III et al. |
| 6,002,859 A | 12/1999 | DiGioia, III et al. |
| 6,068,658 A | 5/2000 | Insall et al. |
| 6,090,114 A | 7/2000 | Matsuno et al. |
| 6,096,043 A | 8/2000 | Techiera et al. |
| 6,106,529 A | 8/2000 | Techiera |
| 6,112,109 A | 8/2000 | D'Urso |
| 6,126,690 A | 10/2000 | Ateshian et al. |
| 6,132,447 A | 10/2000 | Dorsey |
| 6,161,080 A | 12/2000 | Aouni-Ateshian et al. |
| 6,171,340 B1 | 1/2001 | McDowell |
| 6,173,200 B1 | 1/2001 | Cooke et al. |
| 6,183,515 B1 | 2/2001 | Barlow et al. |
| 6,205,411 B1 | 3/2001 | DiGioia, III et al. |
| 6,228,121 B1 | 5/2001 | Khalili |
| 6,254,639 B1 | 7/2001 | Peckitt |
| 6,285,902 B1 | 9/2001 | Kienzle, III et al. |
| 6,327,491 B1 | 12/2001 | Franklin et al. |
| 6,343,987 B2 | 2/2002 | Hayama et al. |
| 6,382,975 B1 | 5/2002 | Poirier |
| 6,383,228 B1 | 5/2002 | Schmotzer |
| 6,385,475 B1 | 5/2002 | Cinquin et al. |
| 6,415,171 B1 | 7/2002 | Gueziec et al. |
| 6,458,135 B1 | 10/2002 | Harwin et al. |
| 6,463,351 B1 | 10/2002 | Clynch |
| 6,503,254 B2 | 1/2003 | Masini |
| 6,510,334 B1 | 1/2003 | Schuster et al. |
| 6,514,259 B2 | 2/2003 | Picard et al. |
| 6,520,964 B2 | 2/2003 | Tallarida et al. |
| 6,533,737 B1 | 3/2003 | Brosseau et al. |
| D473,307 S | 4/2003 | Cooke |
| 6,540,784 B2 | 4/2003 | Barlow et al. |
| 6,558,426 B1 | 5/2003 | Masini |
| 6,575,980 B1 | 6/2003 | Robie |
| 6,602,259 B1 | 8/2003 | Masini |
| 6,672,870 B2 | 1/2004 | Knapp |
| 6,692,448 B2 | 2/2004 | Tanaka et al. |
| 6,701,174 B1 | 3/2004 | Krause et al. |
| 6,702,821 B2 | 3/2004 | Bonutti |
| 6,711,431 B2 | 3/2004 | Sarin et al. |
| 6,711,432 B1 | 3/2004 | Krause et al. |
| 6,712,856 B1 | 3/2004 | Carignan et al. |
| 6,716,249 B2 | 4/2004 | Hyde |
| 6,738,657 B1 | 5/2004 | Franklin et al. |
| 6,747,646 B2 | 6/2004 | Gueziec et al. |
| 6,770,099 B2 | 8/2004 | Andriacchi et al. |
| 6,772,026 B2 | 8/2004 | Bradbury et al. |
| 6,814,575 B2 | 11/2004 | Poirier |
| 6,905,510 B2 | 6/2005 | Saab |
| 6,905,514 B2 | 6/2005 | Carignan et al. |
| 6,923,817 B2 | 8/2005 | Carson et al. |
| 6,932,842 B1 | 8/2005 | Litschko et al. |
| 6,944,518 B2 | 9/2005 | Roose |
| 6,969,393 B2 | 11/2005 | Pinczewski et al. |
| 6,975,894 B2 | 12/2005 | Wehrli et al. |
| 6,978,188 B1 | 12/2005 | Christensen |
| 7,029,479 B2 | 4/2006 | Tallarida et al. |
| 7,033,360 B2 | 4/2006 | Cinquin et al. |
| 7,039,225 B2 | 5/2006 | Tanaka et al. |
| 7,060,074 B2 | 6/2006 | Rosa et al. |
| 7,074,241 B2 | 7/2006 | McKinnon |
| 7,090,677 B2 | 8/2006 | Fallin et al. |
| 7,094,241 B2 | 8/2006 | Hodorek et al. |
| RE39,301 E | 9/2006 | Bertin |
| 7,104,997 B2 | 9/2006 | Lionberger et al. |
| 7,128,745 B2 | 10/2006 | Masini et al. |
| D532,515 S | 11/2006 | Buttler et al. |
| 7,141,053 B2 | 11/2006 | Rose et al. |
| 7,153,309 B2 | 12/2006 | Huebner et al. |
| 7,166,833 B2 | 1/2007 | Smith |
| 7,172,597 B2 | 2/2007 | Sanford |
| 7,174,282 B2 | 2/2007 | Hollister et al. |
| 7,184,814 B2 | 2/2007 | Lang et al. |
| 7,235,080 B2 | 6/2007 | Hodorek |
| 7,238,190 B2 | 7/2007 | Schon et al. |
| 7,239,908 B1 | 7/2007 | Alexander et al. |
| 7,258,701 B2 | 8/2007 | Aram et al. |
| 7,275,218 B2 | 9/2007 | Petrella et al. |
| 7,309,339 B2 | 12/2007 | Cusick et al. |
| 7,340,316 B2 | 3/2008 | Spaeth et al. |
| 7,359,746 B2 | 4/2008 | Arata |
| 7,383,164 B2 | 6/2008 | Aram et al. |

| | | | | | |
|---|---|---|---|---|---|
| 7,388,972 B2 | 6/2008 | Kitson | 2004/0236424 A1 | 11/2004 | Berez et al. |
| 7,393,012 B2 | 7/2008 | Funakura et al. | 2004/0243148 A1 | 12/2004 | Wasielewski |
| 7,394,946 B2 | 7/2008 | Dewaele | 2004/0243481 A1 | 12/2004 | Bradbury et al. |
| 7,429,346 B2 | 9/2008 | Ensign et al. | 2004/0254584 A1 | 12/2004 | Sarin et al. |
| 7,468,075 B2 | 12/2008 | Lang et al. | 2005/0059978 A1 | 3/2005 | Sherry et al. |
| 7,547,307 B2 | 6/2009 | Carson et al. | 2005/0065617 A1 | 3/2005 | Moctezuma de la Barrera |
| 7,611,519 B2 | 11/2009 | Lefevre et al. | 2005/0096535 A1 | 5/2005 | Moctezuma de la Barrera |
| 7,616,800 B2 | 11/2009 | Paik et al. | 2005/0113841 A1 | 5/2005 | Sheldon et al. |
| 7,618,421 B2 | 11/2009 | Axelson, Jr. et al. | 2005/0119664 A1 | 6/2005 | Carignan et al. |
| 7,618,451 B2 | 11/2009 | Berez et al. | 2005/0148843 A1 | 7/2005 | Roose |
| 7,630,750 B2 | 12/2009 | Liang et al. | 2005/0148860 A1 | 7/2005 | Liew et al. |
| 7,634,119 B2 | 12/2009 | Tsougarakis et al. | 2005/0192588 A1 | 9/2005 | Garcia |
| 7,634,306 B2 | 12/2009 | Sarin et al. | 2005/0201509 A1 | 9/2005 | Mostafavi et al. |
| 7,641,660 B2 | 1/2010 | Lakin et al. | 2005/0216024 A1 | 9/2005 | Massoud |
| 7,643,862 B2 | 1/2010 | Schoenefeld | 2005/0234461 A1 | 10/2005 | Burdulis, Jr. et al. |
| 7,693,321 B2 | 4/2010 | Lehtonen-Krause | 2005/0245934 A1 | 11/2005 | Tuke et al. |
| 7,702,380 B1 | 4/2010 | Dean | 2005/0245936 A1 | 11/2005 | Tuke et al. |
| 7,717,956 B2 | 5/2010 | Lang | 2005/0256389 A1 | 11/2005 | Koga et al. |
| D618,796 S | 6/2010 | Cantu et al. | 2005/0267584 A1 | 12/2005 | Burdulis, Jr. et al. |
| 7,747,305 B2 | 6/2010 | Dean et al. | 2006/0015018 A1 | 1/2006 | Jutras et al. |
| D619,718 S | 7/2010 | Gannoe et al. | 2006/0015030 A1 | 1/2006 | Poulin et al. |
| D622,854 S | 8/2010 | Otto et al. | 2006/0015109 A1 | 1/2006 | Haines |
| 7,787,932 B2 | 8/2010 | Vilsmeier et al. | 2006/0015188 A1 | 1/2006 | Grimes |
| 7,794,467 B2 | 9/2010 | McGinley et al. | 2006/0030853 A1 | 2/2006 | Haines |
| D626,234 S | 10/2010 | Otto et al. | 2006/0036257 A1 | 2/2006 | Steffensmeier |
| 7,806,896 B1 | 10/2010 | Bonutti | 2006/0110017 A1 | 5/2006 | Tsai et al. |
| 7,842,039 B2 | 11/2010 | Hodorek et al. | 2006/0111628 A1 | 5/2006 | Tsai et al. |
| 7,842,092 B2 | 11/2010 | Otto et al. | 2006/0122491 A1 | 6/2006 | Murray et al. |
| 7,881,768 B2 | 2/2011 | Lang et al. | 2006/0155293 A1 | 7/2006 | McGinley et al. |
| 7,894,650 B2 | 2/2011 | Weng et al. | 2006/0155294 A1 | 7/2006 | Steffensmeier et al. |
| 7,927,335 B2 | 4/2011 | Deffenbaugh et al. | 2006/0195113 A1 | 8/2006 | Masini |
| 7,940,974 B2 | 5/2011 | Skinner et al. | 2006/0271058 A1 | 11/2006 | Ashton et al. |
| 7,950,924 B2 | 5/2011 | Brajnovic | 2006/0293681 A1 | 12/2006 | Claypool et al. |
| 7,963,968 B2 | 6/2011 | Dees, Jr. | 2007/0005073 A1 | 1/2007 | Claypool et al. |
| D642,263 S | 7/2011 | Park | 2007/0021838 A1 | 1/2007 | Dugas et al. |
| 8,007,448 B2 | 8/2011 | Moctezuma De La Barrera | 2007/0038059 A1 | 2/2007 | Sheffer et al. |
| 8,036,729 B2 | 10/2011 | Lang et al. | 2007/0055268 A1 | 3/2007 | Utz et al. |
| 8,059,878 B2 | 11/2011 | Feilkas et al. | 2007/0073305 A1 | 3/2007 | Lionberger et al. |
| 8,077,950 B2 | 12/2011 | Tsougarakis et al. | 2007/0083266 A1 | 4/2007 | Lang |
| 8,086,336 B2 | 12/2011 | Christensen | 2007/0100462 A1 | 5/2007 | Lang et al. |
| 8,126,533 B2 | 2/2012 | Lavallee | 2007/0106389 A1 | 5/2007 | Croxton et al. |
| RE43,282 E | 3/2012 | Alexander et al. | 2007/0114370 A1 | 5/2007 | Smith et al. |
| 8,133,234 B2 | 3/2012 | Meridew et al. | 2007/0118055 A1 | 5/2007 | McCombs |
| 8,142,189 B2 | 3/2012 | Brajnovic | 2007/0118243 A1 | 5/2007 | Schroeder et al. |
| 8,160,345 B2 | 4/2012 | Pavlovskaia et al. | 2007/0123912 A1 | 5/2007 | Carson |
| 8,177,850 B2 | 5/2012 | Rudan et al. | 2007/0162039 A1 | 7/2007 | Wozencroft |
| 8,202,324 B2 | 6/2012 | Meulink et al. | 2007/0167833 A1 | 7/2007 | Redel et al. |
| 8,214,016 B2 | 7/2012 | Lavallee et al. | 2007/0173858 A1 | 7/2007 | Engh et al. |
| 8,221,430 B2 | 7/2012 | Park et al. | 2007/0191741 A1 | 8/2007 | Tsai et al. |
| 8,231,634 B2 | 7/2012 | Mahfouz et al. | 2007/0198022 A1 | 8/2007 | Lang et al. |
| 8,234,097 B2 | 7/2012 | Steines et al. | 2007/0213738 A1 | 9/2007 | Martin et al. |
| 8,241,293 B2 | 8/2012 | Stone et al. | 2007/0219560 A1 | 9/2007 | Hodorek |
| 8,265,949 B2 | 9/2012 | Haddad | 2007/0226986 A1 | 10/2007 | Chi et al. |
| 8,306,601 B2 | 11/2012 | Lang et al. | 2007/0232959 A1 | 10/2007 | Couture et al. |
| 8,311,306 B2 | 11/2012 | Pavlovskaia et al. | 2007/0233136 A1 | 10/2007 | Wozencroft |
| 8,323,288 B2 | 12/2012 | Zajac | 2007/0233140 A1 | 10/2007 | Metzger et al. |
| 8,331,634 B2 | 12/2012 | Barth et al. | 2007/0233141 A1 | 10/2007 | Park et al. |
| 8,337,501 B2 | 12/2012 | Fitz et al. | 2007/0233269 A1 | 10/2007 | Steines et al. |
| 2002/0055783 A1 | 5/2002 | Tallarida et al. | 2007/0239167 A1 | 10/2007 | Pinczewski et al. |
| 2002/0087274 A1 | 7/2002 | Alexander et al. | 2007/0249967 A1 | 10/2007 | Buly et al. |
| 2002/0160337 A1 | 10/2002 | Klein et al. | 2007/0276224 A1 | 11/2007 | Lang et al. |
| 2003/0009167 A1 | 1/2003 | Wozencroft | 2007/0276400 A1 | 11/2007 | Moore et al. |
| 2003/0055502 A1 | 3/2003 | Lang et al. | 2007/0282451 A1 | 12/2007 | Metzger et al. |
| 2003/0176783 A1 | 9/2003 | Hu | 2007/0288030 A1 | 12/2007 | Metzger et al. |
| 2003/0216669 A1 | 11/2003 | Lang et al. | 2008/0004701 A1 | 1/2008 | Axelson et al. |
| 2004/0097952 A1 | 5/2004 | Sarin et al. | 2008/0015433 A1 | 1/2008 | Alexander et al. |
| 2004/0102792 A1 | 5/2004 | Sarin et al. | 2008/0015599 A1 | 1/2008 | D'Alessio et al. |
| 2004/0102866 A1 | 5/2004 | Harris et al. | 2008/0015600 A1 | 1/2008 | D'Alessio et al. |
| 2004/0133276 A1 | 7/2004 | Lang et al. | 2008/0015602 A1 | 1/2008 | Axelson et al. |
| 2004/0138754 A1 | 7/2004 | Lang et al. | 2008/0015606 A1 | 1/2008 | D'Alessio et al. |
| 2004/0146369 A1* | 7/2004 | Kato .................. 409/219 | 2008/0015607 A1 | 1/2008 | D'Alessio et al. |
| 2004/0147927 A1 | 7/2004 | Tsougarakis et al. | 2008/0021299 A1 | 1/2008 | Meulink |
| 2004/0152970 A1 | 8/2004 | Hunter et al. | 2008/0031412 A1 | 2/2008 | Lang et al. |
| 2004/0153066 A1 | 8/2004 | Coon et al. | 2008/0033442 A1 | 2/2008 | Amiot et al. |
| 2004/0153079 A1 | 8/2004 | Tsougarakis et al. | 2008/0058613 A1 | 3/2008 | Lang et al. |
| 2004/0153087 A1 | 8/2004 | Sanford et al. | 2008/0088761 A1 | 4/2008 | Lin et al. |
| 2004/0171924 A1 | 9/2004 | Mire et al. | 2008/0114370 A1 | 5/2008 | Schoenefeld |
| 2004/0204760 A1 | 10/2004 | Fitz et al. | 2008/0147072 A1 | 6/2008 | Park et al. |
| 2004/0220583 A1 | 11/2004 | Pieczynski, II et al. | 2008/0153067 A1 | 6/2008 | Berckmans et al. |

| | | |
|---|---|---|
| 2008/0161815 A1 | 7/2008 | Schoenefeld et al. |
| 2008/0195108 A1 | 8/2008 | Bhatnagar et al. |
| 2008/0215059 A1 | 9/2008 | Carignan et al. |
| 2008/0234685 A1 | 9/2008 | Gjerde |
| 2008/0243127 A1 | 10/2008 | Lang et al. |
| 2008/0257363 A1 | 10/2008 | Schoenefeld et al. |
| 2008/0262624 A1 | 10/2008 | White et al. |
| 2008/0275452 A1 | 11/2008 | Lang et al. |
| 2008/0281328 A1 | 11/2008 | Lang et al. |
| 2008/0281329 A1 | 11/2008 | Fitz et al. |
| 2008/0281426 A1 | 11/2008 | Fitz et al. |
| 2008/0286722 A1 | 11/2008 | Berckmans, III et al. |
| 2008/0287953 A1 | 11/2008 | Sers |
| 2008/0287954 A1 | 11/2008 | Kunz et al. |
| 2008/0312659 A1 | 12/2008 | Metzger et al. |
| 2008/0319491 A1 | 12/2008 | Schoenefeld |
| 2009/0024131 A1 | 1/2009 | Metzger et al. |
| 2009/0087276 A1 | 4/2009 | Rose |
| 2009/0088674 A1 | 4/2009 | Caillouette et al. |
| 2009/0088753 A1 | 4/2009 | Aram et al. |
| 2009/0088754 A1 | 4/2009 | Aker et al. |
| 2009/0088755 A1 | 4/2009 | Aker et al. |
| 2009/0088758 A1 | 4/2009 | Bennett |
| 2009/0088759 A1 | 4/2009 | Aram et al. |
| 2009/0088760 A1 | 4/2009 | Aram et al. |
| 2009/0088761 A1 | 4/2009 | Roose et al. |
| 2009/0088763 A1 | 4/2009 | Aram et al. |
| 2009/0089034 A1 | 4/2009 | Penney et al. |
| 2009/0093816 A1 | 4/2009 | Roose et al. |
| 2009/0112213 A1 | 4/2009 | Heavener et al. |
| 2009/0131941 A1 | 5/2009 | Park et al. |
| 2009/0131942 A1 | 5/2009 | Aker et al. |
| 2009/0138020 A1 | 5/2009 | Park et al. |
| 2009/0151736 A1 | 6/2009 | Belcher et al. |
| 2009/0157083 A1 | 6/2009 | Park et al. |
| 2009/0163923 A1 | 6/2009 | Flett et al. |
| 2009/0222014 A1 | 9/2009 | Bojarski et al. |
| 2009/0222015 A1 | 9/2009 | Park et al. |
| 2009/0222016 A1 | 9/2009 | Park et al. |
| 2009/0222103 A1 | 9/2009 | Fitz et al. |
| 2009/0234217 A1 | 9/2009 | Mire et al. |
| 2009/0248044 A1 | 10/2009 | Amiot et al. |
| 2009/0254093 A1 | 10/2009 | White et al. |
| 2009/0254367 A1 | 10/2009 | Belcher et al. |
| 2009/0270868 A1 | 10/2009 | Park et al. |
| 2009/0274350 A1 | 11/2009 | Pavlovskaia et al. |
| 2009/0276045 A1 | 11/2009 | Lang |
| 2009/0306676 A1 | 12/2009 | Lang et al. |
| 2009/0307893 A1 | 12/2009 | Burdulis, Jr. et al. |
| 2009/0312805 A1 | 12/2009 | Lang et al. |
| 2010/0023015 A1 | 1/2010 | Park |
| 2010/0042105 A1 | 2/2010 | Park et al. |
| 2010/0049195 A1 | 2/2010 | Park et al. |
| 2010/0087829 A1 | 4/2010 | Metzger et al. |
| 2010/0145344 A1 | 6/2010 | Jordan et al. |
| 2010/0152741 A1 | 6/2010 | Park et al. |
| 2010/0160917 A1 | 6/2010 | Fitz et al. |
| 2010/0168754 A1 | 7/2010 | Fitz et al. |
| 2010/0174376 A1 | 7/2010 | Lang |
| 2010/0191242 A1 | 7/2010 | Massoud |
| 2010/0198351 A1 | 8/2010 | Meulink |
| 2010/0209868 A1 | 8/2010 | De Clerck |
| 2010/0228257 A1 | 9/2010 | Bonutti |
| 2010/0256479 A1 | 10/2010 | Park et al. |
| 2010/0274534 A1 | 10/2010 | Steines et al. |
| 2010/0298894 A1 | 11/2010 | Bojarski et al. |
| 2010/0303313 A1 | 12/2010 | Lang et al. |
| 2010/0303317 A1 | 12/2010 | Tsougarakis et al. |
| 2010/0303324 A1 | 12/2010 | Lang et al. |
| 2010/0305574 A1 | 12/2010 | Fitz et al. |
| 2010/0305708 A1 | 12/2010 | Lang et al. |
| 2010/0305907 A1 | 12/2010 | Fitz et al. |
| 2010/0324692 A1 | 12/2010 | Uthgenannt et al. |
| 2010/0329530 A1 | 12/2010 | Lang et al. |
| 2011/0015636 A1 | 1/2011 | Katrana et al. |
| 2011/0029093 A1 | 2/2011 | Bojarski et al. |
| 2011/0029116 A1 | 2/2011 | Jordan et al. |
| 2011/0046735 A1 | 2/2011 | Metzger et al. |
| 2011/0066193 A1 | 3/2011 | Lang et al. |
| 2011/0066245 A1 | 3/2011 | Lang et al. |
| 2011/0071533 A1 | 3/2011 | Metzger et al. |
| 2011/0071581 A1 | 3/2011 | Lang et al. |
| 2011/0087332 A1 | 4/2011 | Bojarski et al. |
| 2011/0087465 A1 | 4/2011 | Mahfouz |
| 2011/0092804 A1 | 4/2011 | Schoenefeld et al. |
| 2011/0092978 A1 | 4/2011 | McCombs |
| 2011/0144760 A1 | 6/2011 | Wong et al. |
| 2011/0160736 A1 | 6/2011 | Meridew et al. |
| 2011/0166578 A1 | 7/2011 | Stone et al. |
| 2011/0166666 A1 | 7/2011 | Meulink et al. |
| 2011/0172672 A1 | 7/2011 | Dubeau et al. |
| 2011/0184526 A1 | 7/2011 | White et al. |
| 2011/0190899 A1 | 8/2011 | Pierce et al. |
| 2011/0213368 A1 | 9/2011 | Fitz et al. |
| 2011/0213373 A1 | 9/2011 | Fitz et al. |
| 2011/0213374 A1 | 9/2011 | Fitz et al. |
| 2011/0213377 A1 | 9/2011 | Lang et al. |
| 2011/0213427 A1 | 9/2011 | Fitz et al. |
| 2011/0213428 A1 | 9/2011 | Fitz et al. |
| 2011/0213429 A1 | 9/2011 | Lang et al. |
| 2011/0213430 A1 | 9/2011 | Lang et al. |
| 2011/0213431 A1 | 9/2011 | Fitz et al. |
| 2011/0218539 A1 | 9/2011 | Fitz et al. |
| 2011/0218584 A1 | 9/2011 | Fitz et al. |
| 2011/0230888 A1 | 9/2011 | Lang et al. |
| 2011/0238073 A1 | 9/2011 | Lang et al. |
| 2011/0266265 A1 | 11/2011 | Lang |
| 2011/0268248 A1 | 11/2011 | Simon et al. |
| 2011/0270072 A9 | 11/2011 | Feilkas et al. |
| 2011/0276145 A1 | 11/2011 | Carignan et al. |
| 2011/0282473 A1 | 11/2011 | Pavlovskaia et al. |
| 2011/0295329 A1 | 12/2011 | Fitz et al. |
| 2011/0295378 A1 | 12/2011 | Bojarski et al. |
| 2011/0313423 A1 | 12/2011 | Lang et al. |
| 2011/0319897 A1 | 12/2011 | Lang et al. |
| 2011/0319900 A1 | 12/2011 | Lang et al. |
| 2012/0029520 A1 | 2/2012 | Lang et al. |
| 2012/0041446 A1 | 2/2012 | Wong et al. |
| 2012/0053591 A1 | 3/2012 | Haines et al. |
| 2012/0065640 A1 | 3/2012 | Metzger et al. |
| 2012/0066892 A1 | 3/2012 | Lang et al. |
| 2012/0071881 A1 | 3/2012 | Lang et al. |
| 2012/0071882 A1 | 3/2012 | Lang et al. |
| 2012/0071883 A1 | 3/2012 | Lang et al. |
| 2012/0072185 A1 | 3/2012 | Lang et al. |
| 2012/0093377 A1 | 4/2012 | Tsougarakis et al. |
| 2012/0101503 A1 | 4/2012 | Lang et al. |
| 2012/0143197 A1 | 6/2012 | Lang et al. |
| 2012/0150243 A9 | 6/2012 | Crawford et al. |
| 2012/0151730 A1 | 6/2012 | Fitz et al. |
| 2012/0158001 A1 | 6/2012 | Burdulis, Jr. et al. |
| 2012/0158002 A1 | 6/2012 | Carignan et al. |
| 2012/0165821 A1 | 6/2012 | Carignan et al. |
| 2012/0191205 A1 | 7/2012 | Bojarski et al. |
| 2012/0191420 A1 | 7/2012 | Bojarski et al. |
| 2012/0192401 A1 | 8/2012 | Pavlovskaia et al. |
| 2012/0197260 A1 | 8/2012 | Fitz et al. |
| 2012/0197408 A1 | 8/2012 | Lang et al. |
| 2012/0215226 A1 | 8/2012 | Bonutti |
| 2012/0230566 A1 | 9/2012 | Dean et al. |
| 2012/0232669 A1 | 9/2012 | Bojarski et al. |
| 2012/0232670 A1 | 9/2012 | Bojarski et al. |
| 2012/0232671 A1 | 9/2012 | Bojarski et al. |
| 2012/0265499 A1 | 10/2012 | Mahfouz et al. |

FOREIGN PATENT DOCUMENTS

| | | |
|---|---|---|
| DE | 10 2005 023 028 A1 | 11/2006 |
| EP | 0097001 A | 12/1983 |
| EP | 0574098 A | 12/1993 |
| EP | 0622052 A | 11/1994 |
| EP | 0908836 A2 | 4/1999 |
| EP | 0908836 A3 | 12/1999 |
| EP | 1059153 A2 | 12/2000 |
| EP | 1486900 | 12/2004 |
| EP | 1 532 939 A1 | 5/2005 |
| GB | 2215610 | 9/1989 |
| GB | 2420717 A | 6/2006 |
| WO | WO 93/25157 | 12/1993 |

| | | |
|---|---|---|
| WO | WO 95/07509 A1 | 3/1995 |
| WO | WO 95/27450 | 10/1995 |
| WO | WO 97/23172 A2 | 7/1997 |
| WO | WO 98/12995 A2 | 4/1998 |
| WO | WO 01/00096 | 1/2001 |
| WO | WO 01/70142 | 9/2001 |
| WO | WO 01/85040 A1 | 11/2001 |
| WO | WO 02/096268 A2 | 12/2002 |
| WO | WO 2004/032806 | 4/2004 |
| WO | WO 2004/049981 | 6/2004 |
| WO | WO 2005/051240 | 6/2005 |
| WO | WO 2005/087125 A2 | 9/2005 |
| WO | WO 2006/058057 | 6/2006 |
| WO | WO 2006/060795 | 6/2006 |
| WO | WO 2006/092600 | 9/2006 |
| WO | WO 2006/134345 A1 | 12/2006 |
| WO | WO 2007/014164 | 2/2007 |
| WO | WO 2007/058632 A1 | 5/2007 |
| WO | WO 2007/092841 A2 | 8/2007 |

OTHER PUBLICATIONS

Eisenhart-Rothe et al., "The Role of Knee alignment in Disease Progression and Functional Decline in Knee Osteoarthritis," JAMA 2001, 286:188-95.

Elias et al., "A Correlative Study of the Geometry and anatomy of the Distal Femur," Clin orthop Relat Res. 1990(260):98-103.

Favorito et al., "total Knee Arthroplasty in the Valgus Knee," Journal Am Acad Orthop surg. 2002;10(1):16-24.

Freeman et al., "The Movement of the Knee Studied by Magnetic Resonance Imaging," Clinical orthop Relat Res. 2003(410):35-43.

Freeman et al., "The Movement of the Normal Tibio-Femoral Joint," Journal Biomech. 2005;38(2):197-208.

Graichen et al., "Quantitative Assessment of Cartilage Status in Osteoarthritis by Quantitative Magnetic Resonance Imaging: Technical Validation for Use in analysis of Cartilage Volume and Further Morphologic Parameters," Arthritis Rheum 2004, 50:811-16.

Gruen et al., "Least Squares 3D Surface and Curve Matching," ISPRS Journal of Photogrammetry & Remote Sensing, 59(2005), 151-174.

Hollister et al., "The Axes of Rotation of the Knee," Clin Orthop Relat Res. 1993(290):259-68.

Howell et al., "Longitudinal Shapes of the Tibia and Femur are Unrelated and Variable," Clinical Orthopaedics and Related Research (2010) 468: 1142-1148.

Howell et al., "Results of an Initial Experience with Custom-Fit Positioning Total Knee Arthroplasty in a Series of 48 Patients," Orthopedics, 2008;31(9):857-63.

Howell et al., "In Vivo Adduction and Reverse Axial Rotation (External) of the Tibial Component can be Minimized During Standing and Kneeling," Orthopedics, In Press.

Iwaki et al., "Tibiofemoral Movement 1: The Shapes and Relative Movements of the Femur and Tibia in the Unloaded Cadaver Knee," Journal Bone Joint Surg Br. 2000;82(8):1189-95.

Jacobs et al., "Hip Resurfacing Through an Anterolateral Approach," J. Bone Joint Surg Am. 2008:90 Suppl 3:38-44.

Johnson, "Joint Remodeling as the Basis for Osteoarthritis," Journal Am Vet Med Assoc. 1962, 141:1233-41.

Kass et al., "Active Contour Models," International Journal of Computer Vision, pp. 321-331 (1988).

Kellgren et al., "Radiological Assessment of Osteoarthrosis," Ann Rheum Dis 1957, 10:494-501.

Kessler et al, "Sagittal Curvature of Total Knee Replacements Predicts in vivo Kinematics," Clin Biomech (Bristol, Avon) 2007; 22(1):52-8.

Kienzel III et al., "Total Knee Replacement," IEEE May/Jun. 1995.

Kienzel III et al., "An Integrated CAD-Robotics System for Total Knee Replacement Surgery", IEEE International Conference, pp. 889-894, vol. 1, May 1993.

Krackow et al., "Flexion-Extension Joint Gap Changes After Lateral Structure Release for Valgus Deformity Correction in Total Knee Arthroplasty: A Cadaveric Study," Journal Arthroplasty, 1999;14(8):994-1004.

Krackow et al., "Primary Total Knee Arthroplasty in Patients with Fixed Valgus Deformity," Clin Orthop Relat Res. 1991(273):9-18.

Krackow, "Approaches to Planning lower Extremity alignment for Total Knee arthroplasty and Osteotomy About the Knee," adv Orthop surg 7:69, 1983.

Kusumoto et al., "Application of Virtual Reality Force Feedback Haptic Device for Oral Implant Surgery", Graduate School of Dentistry Course for Integrated Oral Science and Stomatology, Jun. 16, 2005.

Akenine-Möller et al., *Real-Time Rendering, Second Edition*, AK Peters, Natick, MA, 6 pages (Table of Contents), 2002.

Author Unknown, "MRI Protocol Reference," ConforMIS, Inc., copyright 2007, http://www.conformis.com/Imaging-Professionals/MRI-Protocol-Guides, last visited on Mar. 28, 2008, 18 pages.

Author Unknown, "MRI Protocol Reference Guide for GE Systems," ConforMIS, Inc., copyright 2007, http://www.conformis.com/Imaging-Professionals/MRI-Protocol-Guides, last visited on Mar. 28, 2008, 18 pages.

Author Unknown, "MRI Protocol Reference Guide for Phillips Systems," ConforMIS, Inc., copyright 2007, http://www.conformis.com/Imaging-Professionals/MRI-Protocol-Guides, last visited on Mar. 28, 2008, 19 pages.

Author Unknown, "MRI Protocol Reference Guide for Siemens Systems," ConforMIS, Inc., copyright 2007, http://www.conformis.com/Imaging-Professionals/MRI-Protocol-Guides, last visited on Mar. 28, 2008, 18 pages.

Barequet et al., "Filling Gaps in the Boundary of a Polyhedron," *Computer Aided Geometric Design*, vol. 12, pp. 207-229, 1995.

Barequet et al., "Repairing CAD Models," Proceedings of the 8th IEEE Visualization '97 Conference, pp. 363-370, Oct. 1997.

Berry et al., "Personalised image-based templates for intra-operative guidance," *Proc. Inst. Mech. Eng. Part H: J. Engineering in Medicine*, vol. 219, pp. 111-118, Oct. 7, 2004.

Biščević et al., "Variations of Femoral Condyle Shape," *Coll. Antropol.*, vol. 29 No. 2, pp. 409-414, 2005.

Blinn, *Jim Blinn's Corner—A Trip Down the Graphics Pipeline*, Morgan Kaufmann Publishers, Inc., San Francisco, CA, 5 pages (Table of Contents), 1996.

Bøhn et al., "A Topology-Based Approach for Shell-Closure," *Geometric Modeling for Product Realization* (P.R. Wilson et al. editors), pp. 297-319, Elsevier Science Publishers B.V., North-Holland, 1993.

Chauhan et al., "Computer-assisted knee arthroplasty versus a conventional jig-based technique—a randomised, prospective trial," *The Journal of Bone and Joint Surgery*, vol. 86-B, No. 3, pp. 372-377, Apr. 2004.

Cohen et al., *Radiosity and Realistic Image Synthesis*, Academic Press Professional, Cambridge, MA, 8 pages (Table of Contents), 1993.

Couglin et al., "Tibial Axis and Patellar Position Relative to the Femoral Epicondylar Axis During Squatting," *The Journal of Arthroplasty*, vol. 18, No. 8, Elsevier, 2003.

Delp et al., "Computer Assisted Knee Replacement," *Clinical Orthopaedics and Related Research*, No. 354, pp. 49-56, Sep. 1998.

Dutré et al., *Advanced Global Illumination*, AK Peters, Natick, MA, 5 pages (Table of Contents), 2003.

Eckhoff et al., "Three-Dimensional Mechanics, Kinematics, and Morphology of the Knee Viewed in Virtual Realty," *The Journal of Bone and Joint Surgery*, vol. 87-A, Supplement 2, pp. 71-80, 2005.

Erikson, "Error Correction of a Large Architectural Model: The Henderson County Courthouse," Technical Report TR95-013, Dept. of Computer Science, University of North Carolina at Chapel Hill, pp. 1-11, 1995.

Ervin et al., *Landscape Modeling*, McGraw-Hill, New York, NY, 8 pages (Table of Contents), 2001.

Farin, *NURB Curves and Surfaces: From Projective Geometry to Practical Use*, AK Peters, Wellesley, MA, 7 pages (Table of Contents), 1995.

Fleischer et al., "Accurate Polygon Scan Conversion Using Half-Open Intervals," *Graphics Gems III*, pp. 362-365, code: pp. 599-605, 1992.

Foley et al., *Computer Graphics: Principles and Practice*, Addison-Wesley Publishing Company, Reading, MA, 9 pages (Table of Contents), 1990.

Glassner (editor), *An Introduction to Ray Tracing*, Academic Press Limited, San Diego, CA, 4 pages (Table of Contents), 1989.

Glassner, *Principles of Digital Image Synthesis*, Volumes One and Two, Morgan Kaufmann Publishers, Inc., San Francisco, CA, 32 pages (Table of Contents), 1995.

Gooch et al., *Non-Photorealistic Rendering*, AK Peters, Natick, MA, 4 pages (Table of Contents), 2001.

Grüne et al., "On numerical algorithm and interactive visualization for optimal control problems," *Journal of Computation and Visualization in Science*, vol. 1, No. 4, pp. 221-229, Jul. 1999.

Guéziec et al., "Converting Sets of Polygons to Manifold Surfaces by Cutting and Stitching," Proc. IEEE Visualization 1998, pp. 383-390, Oct. 1998.

Hafez et al., "Patient Specific Instrumentation for TKA: Testing the Reliability Using a Navigational System," MIS Meets CAOS Symposium & Instructional Academy, Less and Minimally Invasive Surgery for Joint Arthroplasty: FACT and FICTION Syllabus, San Diego, CA, 8 pages, Oct. 20-22, 2005.

Hafez et al., "Computer Assisted Total Knee Replacement: Could a Two-Piece Custom Template Replace the Complex Conventional Instrumentations?", *Computer Aided Surgery*, vol. 9, No. 3, pp. 93-94, 2004.

Hafez et al., "Computer-Assisted Total Knee Arthroplasty Using Patient-Specific Templating," *Clinical Orthopaedics and Related Research*, No. 0, pp. 1-9, 2006.

Jensen, *Realistic Image Synthesis Using Photon Mapping*, AK Peters, Natick, MA, 7 pages (Table of Contents), 2001.

Jones et al., "A new approach to the construction of surfaces from contour data," *Computer Graphics Forum*, vol. 13, No. 3, pp. 75-84, 1994 [ISSN 0167-7055].

Khorramabadi, "A Walk Through the Planned CS Building," Technical Report UCB/CSD 91/652, Computer Science Department, University of California at Berkeley, 74 pages, 1991.

Kidder et al., "3-D Model Acquisition, Design, Planning and Manufacturing of Orthopaedic Devices: A Framework," *Advanced Sensor and Control-System Interface* (B.O. Nnaji editor), Proceedings SPIE—The International Society for Optical Engineering, Bellingham, WA, vol. 2911, pp. 9-22, Nov. 21-22, 1996.

Kumar, *Robust Incremental Polygon Triangulation for Surface Rendering*, Center for Geometric Computing, Department of Computer Science, Johns Hopkins University, Baltimore, MD, WSCG, The International Conference in Central Europe on Computer Graphics, Visualization and Computer Vision, pp. 381-388, 2000.

Lorensen et al., "Marching Cubes: A High Resolution 3d Surface Construction Algorithm," *Computer Graphics*, vol. 21, No. 4, pp. 163-169, 1987.

Nooruddin et al., Simplification and Repair of Polygonal Models Using Volumetric Techniques, *IEEE Transactions on Visualization and Computer Graphics*, vol. 9, No. 2, pp. 191-205, Apr.-Jun. 2003.

Pharr et al., *Physically Based Rendering, from Theory to Implementation*, Morgan Kaufmann Publishers, San Francisco, CA, 13 pages (Table of Contents), 2004.

Platt et al., "Mould Arthroplasty of the Knee, A Ten-Year Follow-up Study," *The Journal of Bone and Joint Surgery* (British Volume), vol. 51-B, No. 1, pp. 76-87, Feb. 1969.

Potter, "Arthroplasty of the Knee with Tibial Metallic Implants of the McKeever and Macintosh Design," *The Surgical Clinics of North America*, vol. 49, No. 4, pp. 903-915, Aug. 1969.

Radermacher et al., "Computer Assisted Orthopaedic Surgery with Image Based Individual Templates," *Clinical Orthopaedics and Related Research*, vol. 354, pp. 28-38, Sep. 1998.

Rohlfing et al., "Quo Vadis, Atlas-Based Segmentation?", *The Handbook of Medical Image Analysis: Segmentation and Registration Models* (Kluwer), pp. 1-55, (http://www.stanford.edu/~rohlfing/publications/2005-rohlfing-chapter-quo_vadis_atlas_based_segmentation.pdf).

Shirley et al., *Realistic Ray Tracing, Second Edition*, AK Peters, Natick, MA, 7 pages (Table of Contents), 2003.

Strothotte et al., *Non-Photorealistic Computer Graphics—Modeling, Rendering, and Animation*, Morgan Kaufmann Publishers, San Francisco, CA, 9 pages (Table of Contents), 2002.

Vande Berg et al., "Assessment of Knee Cartilage in Cadavers with Dual-Detector Spiral CT Arthrography and MR Imaging," *Radiology*, vol. 222, No. 2, pp. 430-436, Feb. 2002.

Wikipedia, the Free Encyclopedia, "CNC," (date unknown) located at http://en.wikipedia.org/wiki/CNC>, 6 pages, last visited on Apr. 12, 2007.

Office Action, U.S. Appl. No. 10/146,862, mailed Jan. 13, 2005, 10 pages.

Amendment and Response to Office Action and Petition to Revive, U.S. Appl. No. 10/146,862, filed Jan. 18, 2006, 29 pages.

International Search Report and Written Opinion, PCT/US2007/001624, dated Dec. 12, 2007, 14 pages.

Invitation to Pay Additional Fees mailed on Jul. 31, 2007, for PCT Application No. PCT/US2007/001624 filed on Jan. 19, 2007, 5 pages.

International Search Report and Written Opinion, PCT/US2007/001622, dated Jun. 11, 2007, 14 pages.

Restriction Requirement, U.S. Appl. No. 11/641,569, mailed Apr. 27, 2009, 7 pages.

International Search Report and Written Opinion, International Application No. PCT/US2009/34983, mailed May 22, 2009, 15 pages.

International Search Report and Written Opinion, International Application No. PCT/US2009/034967, mailed Jun. 16, 2009, 15 pages.

International Search Report and Written Opinion, International Application No. PCT/US2009/041519, mailed Jun. 17, 2009, 10 pages.

Kunz et al., "Computer Assisted Hip Resurfacing Using Individualized Drill Templates," The Journal of Arthroplasty, vol. 00, No. 0, pp. 1-7, 2009.

U.S. Appl. No. 13/086,275, filed Apr. 13, 2011, Park et al.

U.S. Appl. No. 13/066,568, filed Apr. 18, 2011, Pavlovskaia et al.

U.S. Appl. No. 29/394,882, filed Jun. 22, 2011, Ilwhan Park.

International Search Report and Written Opinion, International Application No. PCT/US2009/040629, mailed Aug. 6, 2009, 9 pages.

Restriction Requirement, U.S. Appl. No. 11/641,382, mailed Sep. 3, 2009, 6 pages.

Restriction Requirement, U.S. Appl. No. 11/642,385, mailed Oct. 27, 2009, 7 pages.

International Search Report and Written Opinion, International Application No. PCT/US2009/051109, mailed Nov. 6, 2009, 13 pages.

NonFinal Office Action, U.S. Appl. No. 11/641,569, mailed Nov. 12, 2009, 9 pages.

Restriction Requirement, U.S. Appl. No. 11/656,323, mailed Nov. 13, 2009, 10 pages.

Final Office Action, U.S. Appl. No. 11/959,344, mailed Oct. 27, 2011, 12 pages.

Non-Final Office Action, U.S. Appl. No. 12/390,667, dated Aug. 24, 2011, 49 pages.

Non-Final Office Action, U.S. Appl. No. 12/391,008, mailed Oct. 31, 2011, 44 pages.

Notice of Allowance, U.S. Appl. No. 13/066,568, mailed Oct. 26, 2011, 28 pages.

Response to Restriction Requirement, U.S. Appl. No. 12/391,008, filed Aug. 29, 2011, 9 pages.

Response to Restriction, U.S. Appl. No. 11/946,002, filed Sep. 23, 2011, 7 pages.

Restriction Requirement, U.S. Appl. No. 11/946,002, dated Sep. 1, 2011, 8 pages.

Restriction Requirement, U.S. Appl. No. 12/386,105, dated Oct. 24, 2011, 7 pages.

Restriction Requirement, U.S. Appl. No. 12/391,008, dated Aug. 18, 2011, 6 pages.

U.S. Appl. No. 12/386,105, filed Apr. 14, 2009, Pavlovskaia et al.

U.S. Appl. No. 12/505,056, filed Jul. 17, 2009, Park.

International Search Report and Written Opinion, International Patent Application No. PCT/US2008/083125, dated Mar. 9, 2009, 13 pages.

U.S. Appl. No. 13/374,960, filed Jan. 25, 2012, Pavlovskaia et al.

Final Office Action, U.S. Appl. No. 11/641,569, mailed Mar. 1, 2012, 12 pages.

Non-Final Office Action, U.S. Appl. No. 11/641,382, mailed Mar. 29, 2012, 24 pages.

Non-Final Office Action, U.S. Appl. No. 12/386,105, dated Feb. 9, 2012, 30 pages.
Notice of Allowance, U.S. Appl. No. 11/959,344, mailed Mar. 5, 2012, 13 pages.
Office Action (Restriction Requirement), U.S. Appl. No. 12/563,809, dated Feb. 2, 2012, 7 pages.
Response to final Office Action, U.S. Appl. No. 12/390,667, filed Mar. 12, 2012, 19 pages.
Response to Non-Final Office Action, U.S. Appl. No. 12/391,008, filed Feb. 24, 2012, 18 pages.
Response to Non-Final Office Action, U.S. Appl. No. 11/946,002, filed Mar. 8, 2012, 16 pages.
Response to Restriction Requirement, U.S. Appl. No. 12/563,809, filed Feb. 24, 2012, 10 pages.
Response to Restriction Requirement, U.S. Appl. No. 12/111,924, filed Apr. 16, 2012, 8 pages.
Response to Restriction Requirement, U.S. Appl. No. 12/636,939, filed Apr. 19, 2012, 6 pages.
Response to Restriction, U.S. Appl. No. 12/505,056, filed Apr. 11, 2012, 9 pages.
Restriction Requirement, U.S. Appl. No. 12/111,924, mailed Mar. 19, 2012, 8 pages.
Restriction Requirement, U.S. Appl. No. 12/505,056, mailed Mar. 14, 2012, 8 pages.
Restriction Requirement, U.S. Appl. No. 12/636,939, mailed Apr. 13, 2012, 6 pages.
Response to Non-Final Office Action, U.S. Appl. No. 12/390,667, filed Nov. 18, 2011, 16 pages.
Response to Non-Final Office Action, U.S. Appl. No. 11/641,569, filed Dec. 2, 2011, 7 pages.
Non-Final Office Action, U.S. Appl. No. 11/946,002, dated Nov. 25, 2011, 44 pages.
Response to Restriction Requirement, U.S. Appl. No. 12/386,105, filed Dec. 21, 2011, 9 pages.
Response to Final Office Action, U.S. Appl. No. 11/959,344, filed Dec. 27, 2011, 16 pages.
Final Office Action, U.S. Appl. No. 12/390,667, mailed Jan. 13, 2012, 27 pages.
U.S. Appl. No. 13/488,505, filed Jun. 5, 2012, Ilwhan Park et al.
Advisory Action, U.S. Appl. No. 11/642,385, dated Oct. 29, 2010, 3 pages.
Amendment and Response to Ex Parte Quayle Action, U.S. Appl. No. 29/296,687 dated Mar. 24, 2011, 17 pages.
Amendment and Response to Final Office Action, U.S. Appl. No. 11/642,385, filed Oct. 4, 2010, 16 pages.
Amendment and Response to Non-Final Office Action, U.S. Appl. No. 11/641,382, dated Apr. 20, 2010, 23 pages.
Amendment and Response to Non-Final Office Action, U.S. Appl. No. 11/959,344, dated Jul. 15, 2011, 13 pages.
Amendment and Response to Office Action, U.S. Appl. No. 11/656,323, filed Jun. 25, 2010, 7 pages.
Amendment and Response to Office Action, U.S. Appl. No. 11/641,569, dated Feb. 5, 2010, 20 pages.
Amendment and Response to Restriction Requirement, U.S. Appl. No. 11/641,569, dated May 27, 2009, 12 pages.
Amendment and Response to Restriction Requirement, U.S. Appl. No. 11/641,382, dated Oct. 5, 2009, 10 pages.
Amendment and Response to Restriction Requirement, U.S. Appl. No. 11/642,385, filed Nov. 24, 2009, 10 pages.
Amendment and Response to Restriction/Election Requirement, U.S. Appl. No. 11/656,323, filed Dec. 8, 2009, 6 pages.
Amendment and Response, U.S. Appl. No. 11/642,385, filed May 28, 2010, 11 pages.
European Search Report, 10192631.9-2310, dated Mar. 17, 2011, 5 pages.
Ex Parte Quayle Action, U.S. Appl. No. 29/296,687, mailed Jan. 24, 2011, 11 pages.
Final Office Action and PTO-892, U.S. Appl. No. 11/641,382, mailed Aug. 5, 2010, 13 pages.
Final Office Action and PTO-892, U.S. Appl. No. 11/656,323, mailed Sep. 3, 2010, 11 pages.
Final Office Action, U.S. Appl. No. 11/641,569, mailed May 10, 2010, 9 pages.

International Search Report and Written Opinion, International Application No. PCT/US2009/058946, mailed Jan. 28, 2010, 14 pages.
International Search Report and Written Opinion, International Application No. PCT/US2009/068055, mailed Mar. 11, 2010, 10 pages.
International Search Report and Written Opinion, PCT/US2011/032342, dated Jul. 1, 2011, 8 pages.
Non-Final Office Action and PTO-892, U.S. Appl. No. 11/641,382, mailed Jan. 20, 2010, 12 pages.
NonFinal Office Action and PTO-892, U.S. Appl. No. 11/642,385, mailed Mar. 2, 2010, 11 pages.
Non-Final Office Action and PTO-892, U.S. Appl. No. 11/656,323, mailed Mar. 30, 2010, 10 pages.
Nonfinal Office Action, U.S. Appl. No. 11/959,344, dated Feb. 15, 2011, 29 pages.
Non-Final Office Action, U.S. Appl. No. 11/641,569, dated Aug. 3, 2011, 14 pages.
Notice of Allowance, U.S. Appl. No. 29/296,687, mailed Mar. 31, 2011, 18 pages.
Notice of Non-Compliant Amendment, U.S. Appl. No. 11/641,569, mailed Aug. 7, 2009, 3 pages.
Preliminary Amendment, U.S. Appl. No. 11/641,569, dated Aug. 14, 2008, 13 pages.
Preliminary Amendment, U.S. Appl. No. 11/642,385, filed Aug. 22, 2008, 42 pages.
RCE/Amendment, U.S. Appl. No. 11/641,569, filed Aug. 9, 2010, 18 pages.
RCE/Amendment, U.S. Appl. No. 11/641,382, filed Oct. 26, 2010, 14 pages.
RCE/Amendment, U.S. Appl. No. 11/642,385, filed Dec. 6, 2010, 13 pages.
RCE/Amendment, U.S. Appl. No. 11/656,323, filed Nov. 19, 2010, 12 pages.
Response to Notice of Non-Complaint Amendment, U.S. Appl. No. 11/641,569, dated Aug. 19, 2009, 11 pages.
Response to Restriction Requirement U.S. Appl. No. 29/296,687, filed Oct. 7, 2010, 3 pages.
Response to Restriction Requirement, U.S. Appl. No. 11/959,344, filed Nov. 24, 2010, 13 pages.
Response to Restriction Requirement, U.S. Appl. No. 12/390,667, dated Jul. 27, 2011, 8 pages.
Restriction Requirement, U.S. Appl. No. 11/959,344, dated Oct. 29, 2010, 6 pages.
Restriction Requirement, U.S. Appl. No. 29/296,687, mailed Sep. 21, 2010, 7 pages.
Restriction Requirement, U.S. Appl. No. 12/390,667, dated Jul. 14, 2011, 9 pages.
Akca, "Matching of 3D Surfaces and Their Intensities," ISPRS Journal of Photogrammetry & Remote Sensing, 62(2007), 112-121.
Arima et al., "Femoral Rotational Alignment, Based on the Anteroposterior Axis, in Total Knee Arthroplasty in a Valgus Knee. A Technical Note," Journal Bone Joint Surg Am. 1996;77(9):1331-4.
Bargar et al., "Robotic Systems in Surgery," Orthopedic and Spine Surgery, Surgical Technology International II, 1993, 419-423.
Besl et al., "A Method for Registration of 3-D Shapes," IEEE Transactions on Pattern Analysis and Machine Intelligence (PAMI), 14(2):239-256, Feb. 1992.
Blaha et al., "Using the Transepicondylar Axis to Define the Sagittal Morphology of the Distal Part of the Femur," J Bone Joint Surg Am. 2002;84-A Suppl 2:48-55.
Bullough et al., "The Geometry of Diarthrodial Joints, Its Physiologic Maintenance and the Possible significance of Age-Related Changes in Geometry-to-Load distribution and the Development of Osteoarthritis," Clin Orthop Rel Res 1981, 156:61-6.
Burgkart et al., "Magnetic Resonance Imaging-Based Assessment of Cartilage Loss in Severe Osteoarthritis: Accuracy, Precision, and Diagnostic Value," Arthritis Rheum 2001, 44:2072-7.
Canny, "A computational Approach to Edge Detection," IEEE Transactions on Pattern Analysis and Machine Intelligence, PAMI 8(6), pp. 679-698 (1986).

Churchill et al., "The Transepicondylar Axis Approximates the Optimal Flexion Axis of the Knee," Clin Orthop Relat Res. 1998(356):111-8.

Cicuttini et al., "Gender Differences in Knee Cartilage Volume as Measured by Magnetic Resonance Imaging," Osteoarthritis Cartilage 1999, 7:265-71.

Cicuttini et al., "Longitudinal Study of the Relationship Between Knee angle and Tibiofemoral cartilage Volume in Subjects with Knee Osteoarthritis," Rheumatology (Oxford) 2004, 43:321-4.

Eckhoff et al., "Difference Between the Epicondylar and Cylindrical Axis of the Knee," Clin Orthop Relat Res. 2007;461:238-44.

Lea et al., "Registration and immobilization in robot-assisted surgery", Journal of Image Guided Surgery, pp. 1-10, 1995.

Manner et al., "Knee Deformity in Congenital Longitudinal Deficiencies of the Lower Extremity," Clin Orthop Relat Res. 2006;448:185-92.

Matsuda et al., "Anatomical Analysis of the Femoral Condyle in Normal and Osteoarthritic Knees," Journal Orthopaedic Res. 2004:22(1):104-9.

Matsuda et al., "Femoral Condyle Geometry in the Normal and Varus Knee," Clinical Orthop Relat Res. 1998(349):183-8.

Messmer et al., "Volumetric Determination of the Tibia Based on 2d Radiographs Using a 2d/3d Database", Dept. of Surgery, Trauma Unit, University Hospital, Bessel, Switzerland, *Computer Aided Surgery* 6:183-194 (2001).

Mihalko et al., The Variability of Intramedullary Alignment of the Femoral Component During Total Knee Arthroplasty, Journal Arthroplasty. 2005;20(1):25-8.

Morvan et al., IVECS, Interactively Correcting .STL Files in a Virtual Environment, Clemson University, Clemson, SC, Proc. Conf. Virtual Design, Aug. 1996.

Panjabi et al., "Errors in Kinematic Parameters of a Planar Joint: Guidelines for Optimal Experimental Design," Journal Biomech. 1982;15(7):537-44.

Perillo-Marcone et al., "Effect of Varus/Valgus Malalignment on Bone Strains in the Proximal Tibia After TKR: An Explicit Finite element Study," Journal Biomechanical Engineering 2007, vol. 129, 1:1-11.

Peterfy et al., "Quantification of articular Cartilage in the Knee with Pulsed Saturation Transfer Subtraction and Fact-Suppressed MR Imaging: Optimization and Validation," Radiology 1994, 192:485-91.

Pinskerova et al., "The Shapes and Relative Movements of the Femur and Tibia at the Knee," Orthopaedics 2000;29 Suppl 1:S3-5.

Rosset et al., "General Consumer Communication Tools for improved Image Management and Communication in Medicine," Journal Digital Imaging, 2005;18(4):270-9.

Shakespeare D., "Conventional Instruments in Total Knee Replacement: What Should We Do With Them?" Knee. 2006;13(1):1-6.

Shepstone et al., "The shape of the Distal Femur: A Palaeopathological Comparison of Eburnated and Non-Eburnated Femora," Ann. Rheum Dis. 1999, 58:72-8.

Siston et al., "The Variability of Femoral Rotational Alignment in Total Knee Arthroplasty," Journal Bone Joint Surg Am. 2005;87(10):2276-80.

Siston et al., "Averaging Different Alignment Axes Improves Femoral Rotational Alignment in Computer-Navigated Total Knee Arthroplasty," Journal Bone Joint Surg Am. 2008;90(10):2098-104.

Soudan et al., "Methods, Difficulties and Inaccuracies in the Study of Human Joint Kinematics and Pathokinematics by the Instant axis Concept. Example: The Knee Joint," Journal Biomech. 1979;12(1):27-33.

Spencer et al., "Initial Experience with Custom-Fit Total Knee Replacement: Intra-operative Events and Long-Leg Coronal alignment," International Orthopaedics (SICOT), 2009:In Press.

Stulberg et al., "Computer- and Robot-Assisted Orthopaedic Surgery", Computer-Integrated Surgery Technology and Clinical Applications, edited by Taylor et al., Massachusetts Institute of Technology, Chapter 27, pp. 373-378, 1996.

Teeny et al., "Primary Total Knee Arthroplasty in Patients with Severe Varus Deformity. A Comparative Study," Clin Orthop Relat Res. 1991(273):19-31.

Wright Medical Technology, Inc., "Prophecy Pre-Operative Naviation Guides Surgical Technique," 2009.

Appeal Brief, U.S. Appl. No. 12/390,667, filed Jul. 12, 2012, 32 pages.

Final Office Action, U.S. Appl. No. 11/641,382, mailed Jul. 25, 2012, 12 pages.

Non-Final Office Action, U.S. Appl. No. 12/111,924, mailed Jun. 29, 2012, 35 pages.

Non-Final Office Action, U.S. Appl. No. 12/546,545, mailed Jul. 19, 2012, 28 pages.

Non-Final Office Action, U.S. Appl. No. 12/636,939, mailed Jul. 20, 2012, 25 pages.

Non-Final Office Action, U.S. Appl. No. 13/374,960, mailed Aug. 1, 2012, 6 pages.

Notice of Allowance, U.S. Appl. No. 12/386,105, mailed Jul. 5, 2012, 11 pages.

Response to Final Office Action, U.S. Appl. No. 11/641,569, filed Jun. 28, 2012, 10 pages.

Response to Non-Final Office Action, U.S. Appl. No. 12/386,105, filed Jun. 8, 2012, 13 pages.

Response to Non-Final Office Action, U.S. Appl. No. 11/641,382, filed Jun. 27, 2012, 12 pages.

Response to Restriction, U.S. Appl. No. 12/563,809, filed Aug. 6, 2012, 10 pages.

Howell et al., "In Vivo Adduction and Reverse Axial Rotation (External) of the Tibial Component can be Minimized During Standing and Kneeling," Orthopedics|ORTHOSupersite.com vol. 32 No. 5, 319-326 (May 2009).

U.S. Appl. No. 13/573,662, filed Oct. 2, 2012, Pavlovskaia et al.

Amendment Under 37 C.F.R. 1.312, U.S. Appl. No. 12/386,105, filed Oct. 1, 2012, 6 pages.

Appeal Brief, U.S. Appl. No. 12/391,008, filed Oct. 16, 2012, 24 pages.

Non-Final Office Action, U.S. Appl. No. 12/390,667, mailed Sep. 26, 2012, 21 pages.

Non-Final Office Action, U.S. Appl. No. 12/563,809, mailed Sep. 21, 2012, 32 pages.

Notice of Allowance, U.S. Appl. No. 11/641,382, mailed Oct. 9, 2012, 9 pages.

Notice of Allowance, U.S. Appl. No. 13/374,960, mailed Nov. 2, 2012, 24 pages.

RCE/Amendment, U.S. Appl. No. 11/946,002, filed Sep. 6, 2012, 38 pages.

Response to Final Office Action, U.S. Appl. No. 11/641,382, filed Sep. 24, 2012, 11 pages.

Response to Non-Final Office Action, U.S. Appl. No. 12/111,924, filed Sep. 28, 2012, 10 pages.

Response to Non-Final Office Action, U.S. Appl. No. 12/636,939, filed Oct. 10, 2012, 8 pages.

Response to Non-Final Office Action, U.S. Appl. No. 12/546,545, filed Oct. 19, 2012, 15 pages.

Final Office Action, U.S. Appl. No. 12/546,545, dated Dec. 20, 2012, 16 pages.

Non-Final Office Action, U.S. Appl. No. 11/641,569, dated Jan. 3, 2013, 12 pages.

Notice of Allowance, U.S. Appl. No. 12/111,924, dated Dec. 24, 2012, 10 pages.

Restriction Requirement, U.S. Appl. No. 13/573,662, mailed Jan. 17, 2013, 6 pages.

Advisory Action and Interview Summary, U.S. Appl. No. 12/390,667, mailed Apr. 27, 2012, 23 pages.

Examiner's Answer in appeal, U.S. Appl. No. 12/391,008, mailed Dec. 13, 2012, 27 pages.

Final Office Action, U.S. Appl. No. 11/946,002, mailed May 9, 2012, 24 pages.

Final Office Action, U.S. Appl. No. 12/391,008, mailed May 17, 2012, 28 pages.

Response to Non-Final Office Action, U.S. Appl. No. 12/563,809, filed Dec. 13, 2012, 15 pages.

Response to Restriction, U.S. Appl. No. 12/546,545, filed Jun. 4, 2012, 7 pages.

Restriction Requirement, U.S. Appl. No. 12/546,545, mailed May 3, 2012, 8 pages.

U.S. Appl. No. 13/723,904, filed Dec. 21, 2012, Park.
U.S. Appl. No. 13/730,467, filed Dec. 28, 2012, Park et al.
U.S. Appl. No. 13/730,585, filed Dec. 28, 2012, Park et al.
U.S. Appl. No. 13/730,608, filed Dec. 28, 2012, Park et al.
U.S. Appl. No. 13/731,697, filed Dec. 31, 2012, Pavlovskaia et al.
U.S. Appl. No. 13/731,850, filed Dec. 31, 2012, Park.
Final Office Action, U.S. Appl. No. 12/563,809, mailed Mar. 7, 2013, 14 pages.
Non-Final Office Action, U.S. Appl. No. 13/086,275, mailed Feb. 7, 2013, 36 pages.
Non-Final Office Action, U.S. Appl. No. 12/546,545, mailed Mar. 13, 2013, 10 pages.
Notice of Allowance, U.S. Appl. No. 11/641,382, mailed Feb. 6, 2013, 14 pages.
Notice of Allowance, U.S. Appl. No. 29/394,882, mailed Feb. 4, 2013, 32 pages.
Notice of Allowance, U.S. Appl. No. 12/111,924, mailed Mar. 11, 2013, 14 pages.
Notice of Allowance, U.S. Appl. No. 13/573,662, mailed Mar. 19, 2013, 34 pages.
Response to Final Office Action, U.S. Appl. No. 12/546,545, filed Feb. 20, 2013, 13 pages.
Response to Final Office Action, U.S. Appl. No. 12/636,939, filed Apr. 8, 2013, 10 pages.
Response to Non-Final Office Action, U.S. Appl. No. 12/390,667, filed Feb. 26, 2013, 36 pages.
Response to Non-Final Office Action, U.S. Appl. No. 11/641,569, filed Apr. 3, 2013, 9 pages.
Response to Restriction Requirement, U.S. Appl. No. 12/760,388, filed Apr. 5, 2013, 7 pages.
Response to Restriction, U.S. Appl. No. 13/573,662, filed Feb. 8, 2013, 8 pages.
Restriction Requirement, U.S. Appl. No. 12/760,388, mailed Mar. 6, 2013, 7 pages.

* cited by examiner

ARTHROPLASTY SYSTEMS AND DEVICES, AND RELATED METHODS

CROSS-REFERENCE TO RELATED APPLICATIONS

This application is related to U.S. Design Patent Application Serial No. 29/296,687 entitled "Arthroplasty Jig Blank," filed Oct. 25, 2007, now U.S. Design Pat. No. D642,263 dated Jul. 26, 2011, and hereby incorporated by reference in its entirety.

TECHNICAL FIELD

Described here are systems, devices, and methods for use in the field of arthroplasty. More specifically, described here are arthroplasty jig blanks and systems and methods that may be used to make arthroplasty jigs, such as custom arthroplasty jigs, from the arthroplasty jig blanks.

BACKGROUND

Arthroplasty is commonly used to repair and replace joints damaged from wear, injury, and/or disease. Common arthroplasty procedures can include joint remodel or repair, or implantation of an artificial joint or joint component or implant. Arthroplasty procedures can be used to repair many different joints and joint-like areas in the body, such as the knee, hip, elbow, shoulder, or spine.

The success of an arthroplasty procedure can often be correlated to the degree of fit between the artificial joint or joint components and the patient's surrounding body structures. That is, improving the fit between an artificial joint component and the surrounding bones, cartilage, and musculature may reduce stress on the affected joint and associated structures. This, in turn, may reduce the likelihood of the patient requiring subsequent joint repair, and may also reduce overall complications experienced by the patient during and/or after the arthroplasty procedure.

In an arthroplasty procedure involving the use of an implant to repair a damaged joint, the damaged joint may be prepared for the implant prior to implantation. For example, in a knee arthroplasty procedure, the femur and/or tibia may be treated (e.g., cut, drilled, reamed and/or resurfaced) to provide one or more surfaces that are configured to receive the implant. Certain surgical tools, such as arthroplasty jigs, may be used to accurately position and/or control one or more of the instruments that are used to provide such treatment, such as saws, drills, reamers, and the like. Arthroplasty jigs may be configured with apertures or slots to control the position, length, and/or depth of the instruments. Moreover, enhanced accuracy and precision may be provided in an arthroplasty procedure by using custom or patient-specific arthroplasty jigs. Such arthroplasty jigs are configured for use in certain anatomical target sites of a particular patient. Examples of arthroplasty jigs, including custom arthroplasty jigs, are disclosed in U.S. patent application Ser. No. 11/641,569, filed Dec. 18, 2006, U.S. patent application Ser. No. 11/642,385, filed Dec. 19, 2006, and U.S. patent application Ser. No. 11/656,323, filed Jan. 19, 2007, each of which is hereby incorporated by reference in its entirety.

It would be desirable to provide methods and/or tools for making arthroplasty jigs, including custom or patient-specific arthroplasty jigs, relatively efficiently. For example, it would be desirable to provide methods that reduce the time and/or cost associated with the fabrication of arthroplasty jigs. It would also be desirable to provide methods that result in enhanced accuracy and precision in the manufacturing of arthroplasty jigs, such as custom arthroplasty jigs.

SUMMARY

Described here are systems and methods that may be used to form arthroplasty jigs from arthroplasty jig blanks. These systems and methods may allow arthroplasty jigs to be manufactured relatively efficiently and/or cost-effectively. Additionally, these systems and methods may provide enhanced positioning and/or stabilization of an arthroplasty jig blank during a machining procedure. This, in turn, may result in the relatively accurate formation of a desired arthroplasty jig. For example, the improved stabilization and positioning of a jig blank during machining may allow for accurate machining of detailed features on a surface of the jig blank, especially features having relatively small dimensions. Thus, by using the systems, methods, and jig blanks described here, the resulting arthroplasty jigs may exhibit improved feature resolution and/or customization. Further, the systems, methods and jig blanks may improve machining accuracy even while decreasing machining time, thereby producing arthroplasty jigs with improved fit and reduced cost.

Some variations of arthroplasty jig manufacturing systems described here comprise a first positioning component and an arm fixture component. The arm fixture component is integral with, or configured to be coupled to, an arthroplasty jig blank body. The first positioning component is integral with, or configured to be coupled to, a machining device, such as a computer numerical control (CNC) machine. Further, the arm fixture component is configured to couple to the first positioning component so that the jig blank body can be positioned for machining by the machining device.

In certain variations, the first positioning component may be configured to position the jig blank body along a plane defined by two translational axes of the machining device when the arm fixture component is coupled to the first positioning component. The arm fixture component may include a first surface and a second surface. When the arm fixture component is coupled to the first positioning component, the first surface may be aligned with one of the translational axes of the machining device, and the second surface may be aligned with another translational axis of the machining device. The translational axes of the machining device may be, for example, X- and Y-axes that define a plane (e.g., a horizontal plane).

In some variations, the first positioning component may be configured to rotate the jig blank around a rotational axis of the machining device when the arm fixture component is coupled to the first positioning component. In certain variations, the arm fixture component may be coupled to the first positioning component, and the first positioning component may position the jig blank body so that a volume of the jig blank body is accessible by one or more machining tools of the machining device. In some systems, a volume of the jig blank body that is at least about 30 cubic inches, or at least about 40 cubic inches, may be accessible by one or more machining tools as the jig blank body is positioned via the arm fixture component coupled to the first positioning component. The arm fixture component may have a dimension of, for example, about 4 inches to about 8 inches.

The arm fixture component may have any suitable shape or configuration. The arm fixture component shape and/or configuration may be selected to provide accurate alignment and mounting of the jig blank body in the positioning component, and/or to maintain the position of the jig blank body even while it is under force and/or torque from machining tools. In some variations, the arm fixture component may comprise a U-shaped member configured to couple to the first positioning component. Certain variations of the systems may include a clamp, one or more screws, a lock, or the like, configured to releasably secure the arm fixture component to the first positioning component.

Variations of the arthroplasty jig manufacturing systems may include a second positioning component. As with the first positioning component, the second positioning component may be integral with, or configured to be coupled to, a machining device, such as a CNC machine. In these systems, the arm fixture component may be configured to be coupled to both the first positioning component and the second positioning component. When the arm fixture component is coupled to both the first and second positioning components, the jig blank body may be positioned for machining by the machining device (e.g., a CNC machine). Here, the arm fixture component may comprise first and second U-shaped members. The first U-shaped member may be configured to couple to the first positioning component, and the second U-shaped member may be configured to couple to the second positioning component. Variations of these systems may include a clamp, one or more screws, a lock, or the like, configured to releasably secure the arm fixture component to the second positioning component.

The arthroplasty jig manufacturing systems described here may be adapted for any suitable application. For example, the systems may be used to manufacture knee, hip, shoulder, elbow, and/or spinal arthroplasty jigs. Correspondingly, the arthroplasty jig blanks used in the systems may comprise knee arthroplasty jig blanks, hip arthroplasty jig blanks, shoulder arthroplasty jig blanks, elbow arthroplasty jig blanks, or spinal arthroplasty jig blanks. In some variations, the arthroplasty jig blanks may be suitable for use in forming multiple different types of arthroplasty jigs. For example, a single arthroplasty jig blank may be used to form either a knee arthroplasty jig or a hip arthroplasty jig.

Also described here are positioning components for positioning a jig blank body of an arthroplasty jig blank in a machining device, such as a CNC machine. The positioning components include a positioning component body that is integral with, or configured to be coupled to, the machining device. The positioning component body comprises a first registration portion that is configured to couple with the arthroplasty jig blank. Coupling the first registration portion with the arthroplasty jig blank positions the jig blank body along or about one or more axes of the machining device to allow for machining of at least a portion of the jig blank body. In certain variations, the positioning component body may be configured to rotate about a first rotational axis of the machining device.

In some variations of the positioning components, the first registration portion is configured to be aligned with a first translational axis of the machining device, and to slidably engage an arm fixture component of the arthroplasty jig blank. Variations of positioning components may comprise a second registration portion configured to be aligned with a second translational axis of the machining device. The second registration portion may abut the arm fixture component when the first registration portion slidably engages the arm fixture component.

Methods for machining arthroplasty jigs are also described. The methods include coupling an arm fixture component of an arthroplasty jig blank to a first positioning component that is coupled to, or integral with, a machining device (e.g., a CNC machine). The first positioning component is adjusted to position a jig blank body of the arthroplasty jig blank along or about one or more axes of the machining device. The methods include machining at least a portion of the jig blank body with one or more machining tools of the machining device to form the arthroplasty jig. Some variations of the methods may include coupling the arm fixture component of the arthroplasty jig blank to a second positioning component that is coupled to, or integral with, the machining device.

In certain methods, the first positioning component is adjusted to position the jig blank body by rotating the first positioning component about a rotational axis of the machining device. In some variations, the first positioning component may be rotated a full 360° about a rotational axis of the machining device. Adjusting the first positioning component to position the jig blank body may comprise translating the first positioning component along one or more translational axes (e.g., an X-axis and/or a Y-axis) that may define a plane (e.g., a horizontal plane).

Further, arthroplasty jig blanks are described herein. The arthroplasty jig blanks include a jig blank body and an arm fixture component that is integral with, or coupled to, the jig blank body. In the arthroplasty jig blanks, the arm fixture component is configured to be coupled to a machining device (e.g., a CNC machine) to position the jig blank body so that at least a portion of the jig blank body can be machined by the machining device. For example, the jig blank body may be rotated about or translated along one or more axes of the machining device to allow machining of at least a portion of the jig blank body. In some variations of the jig blanks, the arm fixture component may be configured to be slidably coupled to a positioning component that, in turn, is coupled to, or integral with, the machining device.

Methods of making an arthroplasty jig blank also are described. These methods include forming a mold, filling the mold with a moldable polymer, curing or setting the polymer in the mold, and releasing the mold to form an arthroplasty jig blank. The arthroplasty jig blank comprises a jig blank body and an arm fixture component integral with, or coupled to, the jig blank body. Any suitable polymer molding technique may be used including, for example, injection molding and/or compression molding. The arm fixture component may be configured to couple to a machining device to allow machining of at least a portion of the jig blank body.

DETAILED DESCRIPTION

Figure 1A:
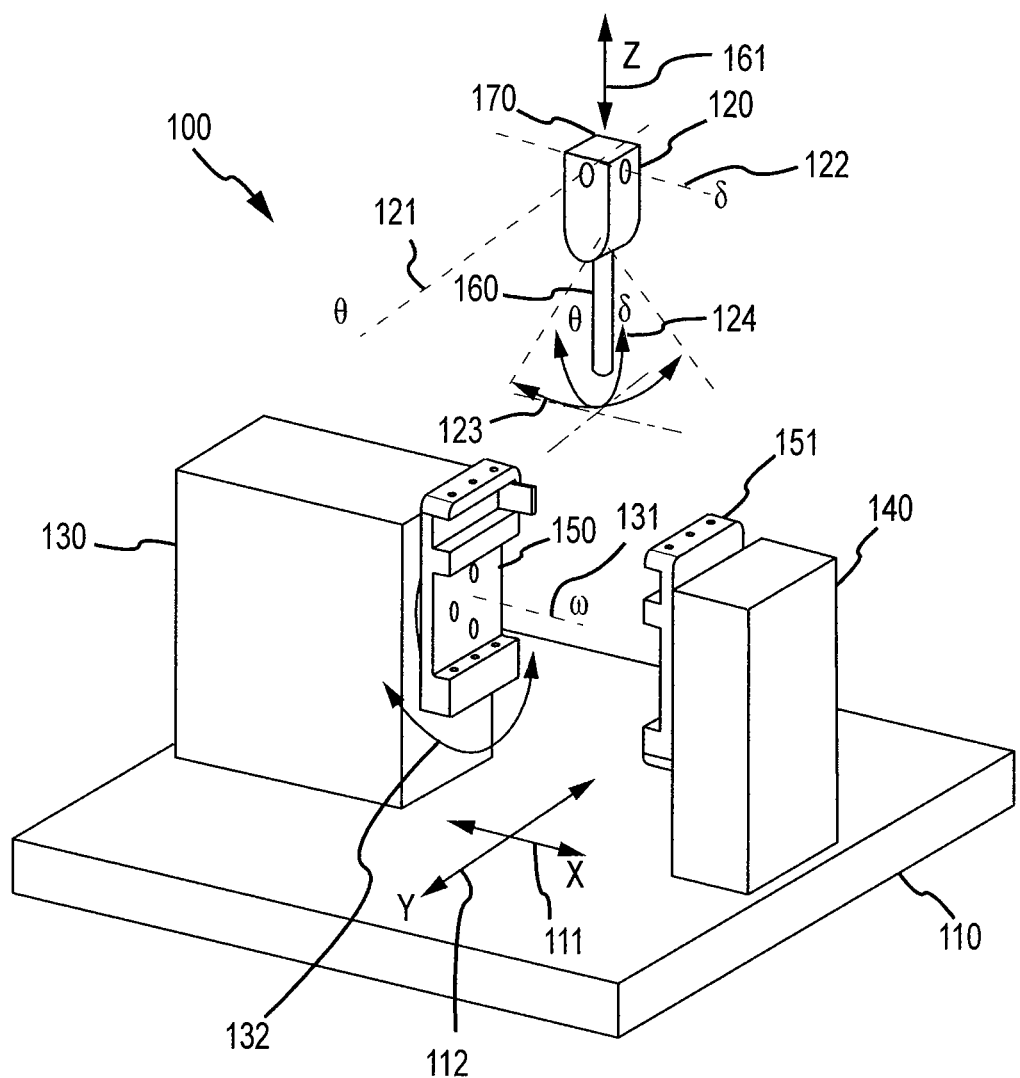
FIG. 1A is a perspective view of a variation of a machining device and two arthroplasty jig blank positioning components.

Described here are systems, methods, arthroplasty jig blanks, and positioning components that can be used in the manufacture of arthroplasty jigs. Non-limiting examples of such arthroplasty jigs include knee arthroplasty jigs, which can be adapted for the tibia and/or the femur, hip arthroplasty jigs, elbow arthroplasty jigs, and spinal arthroplasty jigs. Further, methods for making arthroplasty jig blanks are described.

The methods, systems, and positioning components described here, as well as the arthroplasty jig blank configurations described here, may provide relatively stable mounting of the arthroplasty jig blanks into a machining device. The mounting can allow for rotation and translation of the jig blanks to provide ample machine tool access to the jig blank bodies. In addition, the mounting may provide sufficient stability to secure the positions of the jig blanks, even in the presence of force (e.g., vertical force) and/or torque (rotational force) from the machining process. The relatively stable mounting and positioning may, in turn, allow for relatively accurate machining, even of detailed features, on the jig blank bodies. In addition, all or part of the machining device's coordinate system may be transferred to the jig blank bodies, so that machine files written in the machining device's reference frame may be applied directly to the jig blanks (e.g., without a need for axis conversion or for verification of the jig blanks' positions relative to the machining device). When used with an automated machining device, such as a CNC machine, the systems and methods may provide for the relatively rapid and/or accurate manufacturing of arthroplasty jigs, such as custom arthroplasty jigs. Decreased manufacturing time resulting from the use of the systems and methods described here may lower manufacturing costs, even while the machined arthroplasty jigs exhibit equivalent or improved accuracy in comparison to arthroplasty jigs manufactured using other systems and methods.

As described above, in some variations, custom arthroplasty jigs may be formed. Before fabrication of a custom arthroplasty jig to be used in an arthroplasty procedure for a particular subject (e.g., a patient), the affected joint may be mapped out preoperatively. Imaging techniques, such as computed tomography (CT) or magnetic resonance imaging (MRI), may be used to obtain a series of two-dimensional images to map out the affected region. For knee arthroplasty, the affected region may include the lower (distal) end of the femur and/or the upper (proximal) end of the tibia. The series of two-dimensional images can be used to create a three-dimensional model of the damaged bone region. For example, the three-dimensional model may be created by using the two-dimensional images to determine location coordinate values of each of a sequence of spaced apart surface points along the damaged bone surface. A mathematical computer model may then be used to generate the three-dimensional model. Examples of mathematical computer models that can be used to generate three-dimensional models include Analyze (from AnalyzeDirect, Inc., Overland Park, Kans.), Insight Toolkit (open-source software available from the National Library of Medicine Insight Segmentation and Registration Toolkit (ITK), www.itk.org), and 3D Slicer (open-source software available from www.slicer.org). Other appropriate mathematical computer models may also be used.

After the computer-generated three-dimensional model has been formed, it may be used to generate a machine code or set of instructions for input into a computer numerical control (CNC) machine. The machine code can provide instructions to the CNC machine for selective removal of material from an arthroplasty jig blank to shape and fabricate an arthroplasty jig. Because images of the subject's unique bone structure have been used to generate the machine code, custom arthroplasty jigs may be manufactured.

However, mounting and securing a blank, such as an arthroplasty jig blank, in a machining device such as a CNC machine is important to ensure accuracy, especially for the machining of detailed features having small dimensions (e.g., less than about 2 mm, or less than about 1 mm, or less than about 0.5 mm, or even smaller). In addition, because custom arthroplasty jigs may have complex geometries and/or surface configurations, accessing a workable volume of the jig blank for cutting, milling, drilling and the like without compromising stability or positional accuracy can be difficult. The systems, methods, and jig blanks described here may provide secure mounting in a machining device. They may provide for preservation and transfer of one or more axes of the machining device's coordinate system to the jig blank. As a result, machining instructions provided in the machining device's frame of reference may not need to be transposed into a different set of coordinates, and the position of the jig blank relative to the machining device may not need to be ascertained or verified. That is, a machine code instruction to remove material from the jig blank at a certain location in a specified direction may be provided directly in the machining device's coordinate system. This may simplify the process of generating machining instructions, and also may reduce the likelihood of errors occurring when transposing instructions from one coordinate system to another. It should be pointed out that the methods, systems, positioning components, and arthroplasty jig blanks described here are suitable for use in the manufacture of non-custom arthroplasty jigs (such as arthroplasty jigs that may be used for a variety of different subjects), as well as custom arthroplasty jig blanks (such as arthroplasty jigs that are designed for use for a specific subject).

While a CNC machine is described here, any suitable machining device can be used to form an arthroplasty jig, including an automated machine (e.g., a robotically-operated machine), or a manually-operated machine. CNC machines are available in a variety of configurations, including, for example, CNC drills, CNC milling machines, CNC lathes, CNC saws, and any combination of these machines and/or other machines. An example of a CNC machine that may be used with the systems, methods, and jig blanks described here is a Roland MDX milling machine (e.g., a Roland MDX 650 milling machine or a Roland MDX 540 milling machine).

FIG. 1A illustrates an example of a CNC machine that may be used to form an arthroplasty jig. The CNC machine may machine an arthroplasty jig blank by milling, drilling, cutting, reaming, and/or resurfacing, from multiple angles and sides, according to instructions input into the machine. The CNC machine (100) illustrated in FIG. 1A includes six axes: three translational axes and three rotational axes. However, while CNC machine (100) includes six axes, machining devices with any number of axes (e.g., one, two, three, four, or five, or more than six) may be used. The translational axes for CNC machine (100) are shown as X-axis (111), Y-axis (112), and Z-axis (161). The X-axis and the Y-axis define an X-Y plane. A spindle unit (120) includes a cutting tool (160) and can be translated along Z-axis (161), which is perpendicular to the X-Y plane, as well as along X-axis (111) and along Y-axis (112). The X-Y plane defined by the X- and Y-axes may be generally horizontal, and the Z-axis may be in a generally vertical direction perpendicular to the X-Y plane.

Still referring to FIG. 1A, the first rotational axis ω (131) of CNC machine (100) traces out a rotational path indicated by a double-headed arrow (132). In this example, full 360° rotation around first rotational axis ω (131) is possible. The second rotational axis θ (121) traces out a rotational path shown by a double-headed arrow (123), defining a plane. The third rotational axis δ (122) traces out a path indicated by a double-headed arrow (124), defining a plane perpendicular to that defined by rotation about second rotational axis θ (121). The bottom portion (160) of spindle unit (120) can rotate, and represents a cutting member that can comprise varying sizes of interchangeable machining tools (e.g., drill bits, milling tools, reamers, polishers, and the like). Thus, translational motion of the machining tools in the X-direction, Y-direction, or Z-direction can be accomplished by translating spindle unit (120) in the X-direction, Y-direction, or Z-direction. Alternatively, or in addition, an object to be machined can be translated relative to the machining tool by mounting the object on a movable stage, such as an X-Y stage or an X-Y-Z stage (not shown) provided on or as part of table (110). Rotational motion (e.g., by 360°) about first rotational axis ω (131) is enabled by one or more gears or rotatable shafts coupled to a motor or actuator (not shown) in rotary driver (130). Rotational motion about second rotational axis θ (121) and third rotational axis δ (122) is enabled by one or more gears or rotatable shafts coupled to a motor or actuator coupled to spindle unit (120). As an example, some machines may be capable of 180° rotation or even more about third rotational axis δ (122) or second rotational axis θ (121).

Translational and rotational movement along or about each of the above-described axes may be accomplished by any suitable type of motor or actuator. Non-limiting examples of motors and actuators include electric or electromechanical motors such as stepper motors, servo motors, DC motors, AC motors, and the like, linear, rotary, or semi-rotary actuators (e.g., pneumatic actuators, hydraulic actuators, piezoelectric actuators), and combinations of motors and actuators. For example, a rotary driver unit (130) mounted on a table (110) can include a servo motor to drive rotation about first rotational axis ω (131). Spindle unit (120) can be translated in the X-, Y-, and/or Z-directions, for example, using stepper motors. Spindle unit (120) may also be capable of generating rotation about third rotational axis δ (122), and/or rotation about second rotational axis θ (121), for example, using a semi-rotary drive and/or a semi-rotary actuator. Thus, spindle unit (120) may include a top portion (170) that can be attached to one or more motors or actuators to enable movement along the X-axis, the Y-axis, the Z-axis, the δ-axis, and/or the θ-axis.

As stated above, machining devices with fewer than six axes, or fewer than five axes, may be used. For example, a five-axis CNC machine that does not include one or more of the rotational axes may be used (e.g., a CNC machine that does not include third rotational axis δ (122) as shown in FIG. 1A). In other situations, a four-axis CNC machine that does not include a δ-rotational axis or a θ-rotational axis may be used. Such a CNC machine would include the three translational axes and the ω-rotational axis as shown in FIG. 1A. Of course, machining devices which include fewer than four axes or more than six axes may also be used, as appropriate.

A machining device such as CNC machine (100) may be used, for example, to form an arthroplasty jig from an arthroplasty jig blank. In some instances, the arthroplasty jig may be a custom arthroplasty jig. Because of the complexity of some arthroplasty jigs' surfaces, especially custom arthroplasty jigs, it may be necessary to access multiple surfaces and/or sides of a jig blank from different angles to obtain the desired custom arthroplasty jig. By using the systems described herein, an arthroplasty jig blank can be positioned into a machining device in a way that allows one or more machining tools to access a body of the blank, while also securing the blank against movement even while under force or torque exerted on the blank by the machining process. Moreover, the systems described here may allow the arthroplasty jig blank to be positioned in a way that preserves one or more axes of the coordinate system of the machining device, such that the machine tools can operate and follow instructions in the machining device's reference frame. For example, a machine instruction to begin machining at a particular (X, Y, Z) coordinate in a specified direction may be applied directly to the jig blank, without a need to transpose coordinate systems, or to verify the position of the jig blank relative to the machine tool. Although the systems and methods described here are generally described for use in the manufacture of custom arthroplasty jigs, it is to be understood that the systems and methods can be applied to the manufacture of custom implants as well. Additionally, the systems and methods described here may be used to manufacture non-custom arthroplasty jigs and/or non-custom implants.

In certain variations, an arthroplasty jig manufacturing system may be used to provide enhanced arthroplasty jig manufacturing by a machining device. Generally, the arthroplasty jig manufacturing systems described here comprise a first positioning component. The first positioning component can be integral with, or configured to be coupled to, a machining device, such as a CNC machine similar to that illustrated in FIG. 1A, or a variant thereof. As used here, two components that are "integral with" each other includes two components that are part of a unitary body. Thus, the first positioning component can be formed directly onto a part of the machining device. Alternatively, the first positioning component can be a separate component that is affixed to, or coupled to, a part of the machining device.

The first positioning component can be integral with, or coupled to, any part of the machining device that allows movement of the first positioning component. For example, the first positioning component may be integral with, or coupled to, a shaft that can rotate and/or translate, a shaft that is coupled to a motor or actuator, a mounting plate or mounting surface that can rotate and/or translate, or a mounting plate or mounting surface that is coupled to a motor or actuator. Therefore, a motor or actuator that is part of the machining device can in turn drive motion of the first positioning component. Because movement of the first positioning component is driven by the machining device, the coordinate system of the machining device that includes its translational axes and its rotational axes can be preserved and transferred to the first positioning component. Thus, the coordinate system of the manufacturing device can also be transferred to a jig blank that is properly coupled to the first positioning component, as described below. As a result, instructions based on the machining device's coordinate system may be directly applied to the jig blank, without requiring coordinate system uncertainty or conversion. The result may be simplification and improved accuracy and precision during machining of the jig blank.

Figure 1B:
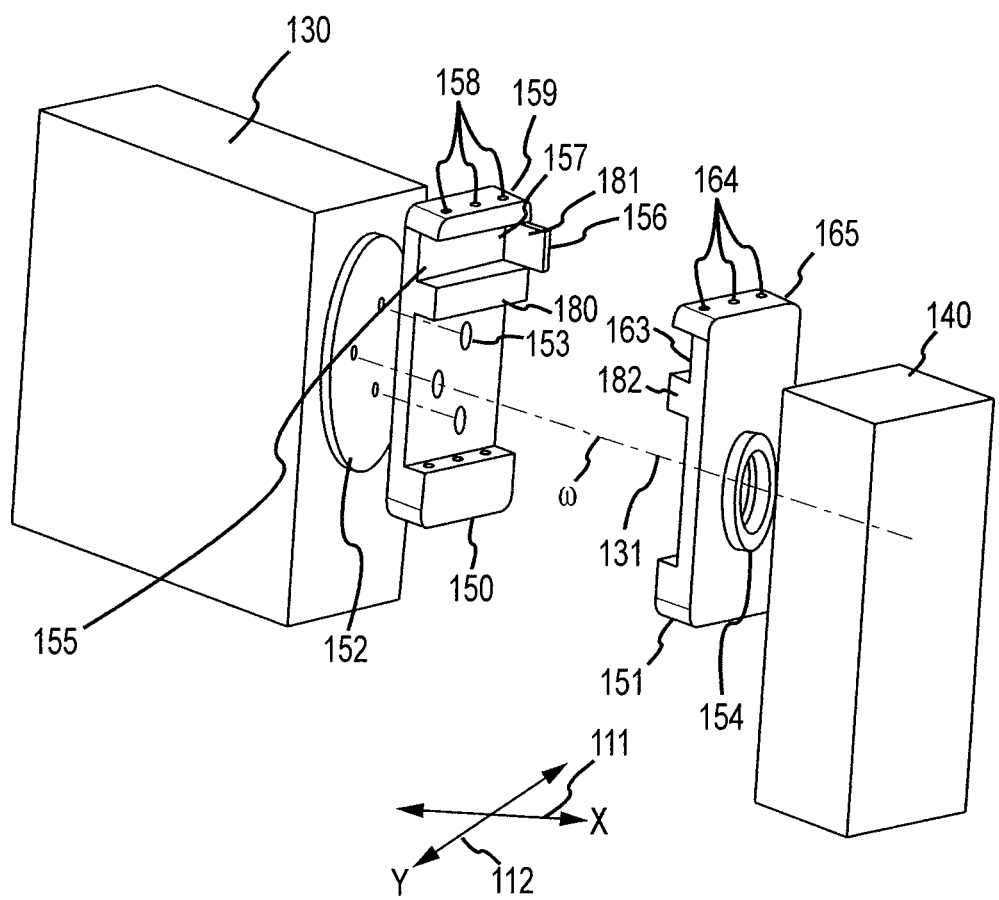
FIG. 1B is an enlarged view of the machining device and arthroplasty jig blank positioning components of FIG. 1A.

A variation of a first positioning component (150) is illustrated in FIG. 1A and again in a more enlarged view in FIG. 1B. First positioning component (150) is coupled to a rotatable shaft (not shown) that is driven by a rotary driver unit (130), so that first positioning component (150) can be rotated about first rotational axis ω (131). First positioning component (150) can be coupled to rotary driver unit (130) by any suitable method (e.g., by clamping, by one or more screws, mechanical locking, or adhesive). More than one securing method may be used, e.g., clamping combined with screws. In the variation shown in FIGS. 1A and 1B, first positioning component (150) is affixed to a mounting plate (152) with mounting screws (153). Mounting plate (152) is coupled to a rotatable shaft that is driven by rotary driver unit (130), so that a center of rotation of first positioning component (150) is aligned with first rotational axis ω (131).

As indicated above, the positioning components that are part of the systems described here are used to position a jig blank body of an arthroplasty jig blank in a machining device. In order to preserve and transfer one or more axes of the machining device coordinate system to the jig blank body, the positioning components can include one or more registration portions that are configured to receive, align and secure a jig blank coupled thereto. Thus, the positioning components have a positioning component body that is integral with, or configured to be coupled to, the machining device, and that comprises a first registration portion configured to couple with the arthroplasty jig blank. Coupling the first registration portion of the positioning component body with the arthroplasty jig blank positions the jig blank body along or about one or more axes of the machining device to allow for machining of at least a portion of the jig blank body.

For example, as shown in FIG. 1B, first positioning component (150) includes a positioning component body (180) that comprises a first registration portion (155) and a second registration portion (156). As shown, first registration portion (155) is in the form of a slot or groove having a surface (157) that can be aligned with a translational axis of the machining device (e.g., Y-axis (112)). Second registration portion (156) is configured as a stop having a surface (181) that also can be aligned with a translational axis of the machining device (e.g., X-axis (111)). It should be pointed out that positioning components with only a single registration portion can be used, where the single registration portion is configured to be aligned with a translational axis of the machining device. Also, positioning components with more than two registration portions may be used, for example a positioning component with three registration portions, each aligned with one of three orthogonal axes. Further, registration portions may contain additional features, such as demarcations indicating a scale, one or more positional stops, and/or one or more positional indicators or sensors.

Although the first registration portion is configured as a slot or groove and the second registration portion is configured as a stop in the illustrative variation shown in FIG. 1B, any suitable registration scheme may be used to receive, align and secure a jig blank that is coupled to it. As an example, a positioning component may include a protrusion that mates with an indentation on an arthroplasty jig blank. For example, a linear protrusion may mate with a slot or groove on the jig blank. As another example, a pin and socket configuration may be used, in which a positioning component includes a socket configured to receive one or more pins on a jig blank, or a jig blank includes a socket configured to receive one or more pins on a positioning component. Further, a single feature in a positioning component can include both a first and a second registration portion. As an example, a positioning component may include a groove parallel to the Y-axis of the machining device, wherein the groove includes a side wall parallel to the X-axis of the machining device.

A positioning component can secure an arthroplasty jig blank so that the position of the arthroplasty jig blank is ascertainable, accurate, and precise during the machining process, which can exert substantial force and/or torque on the jig blank. To that end, a positioning component may include one or more securing devices to secure the jig blank's position. Some variations of positioning components include one or more set screws that can be tightened against the jig blank to releasably secure the jig blank with or in the registration portion of the positioning component. For example, positioning component (150) in FIG. 1B includes set screws (158) that can be tightened from a top side (159) of the positioning component (150) to secure a jig blank (not shown) positioned in registration portion (155). While screws have been shown, a jig blank can be releasably secured in a registration portion of a positioning component using any suitable securing device. Non-limiting examples of such securing devices include clamping devices (e.g., a releasable clamp that is part of the positioning component, or a releasable clamp that is separate from the positioning component), or mechanical locks or brackets, or even adhesives. Combinations of securing devices may be used, e.g., a clamp combined with one or more screws, adhesives, and/or locks. In some cases, the configuration of the registration portion itself may be sufficient to secure the jig blank. For example, the jig blank may have a configuration that interlocks with the registration portion.

Certain variations of the systems described here can include two or more positioning components. For example, FIGS. 1A and 1B show a variation of a second positioning component. In the variation illustrated, the second positioning component (151) is coupled to a stabilizing unit (140) mounted on table (110) of CNC machine (100). In this case, second positioning component (151) is configured to rotate about first rotational axis ω (131). To this end, second positioning component (151) can be coupled to a rotational shaft that rotates about first rotational axis ω (131) in stabilizing unit (140). Second positioning component (151) can be coupled to stabilizing unit (140) using any suitable method (e.g., by screws, mechanical locking, or adhesive). For example, and as shown in FIG. 1B, second positioning component (151) includes a cylindrical member (154) that is configured to be concentric with first rotational axis ω (131) and to mechanically mate or lock with stabilizing unit (140) (e.g., on a mounting plate or mounting surface of the stabilizing unit that is coupled to a rotational shaft to allow rotation about first rotational axis ω (131)). Stabilizing unit (140) need not contain a motor or actuator to drive motion about or along an axis. Rather, stabilizing unit (140) can function to support an object affixed thereto while it is moved. For example, stabilizing unit (140) can contain a rotatable and/or translatable shaft that supports an object during rotation about first rotational axis ω (131) and/or translation along the X-axis and/or Y-axis. In some variations, stabilizing unit (140) may contain one or more motors or actuators to effect motion about or along one or more axes of CNC machine (100).

In systems that include a second positioning component, the second positioning component may comprise one or more registration portions that are configured to receive, align, and secure a jig blank while the jig blank is being positioned and/or machined. Thus, second positioning component (151) in FIG. 1B includes a second positioning component body (182) that comprises first registration portion (163). In the variation shown in FIG. 1B, first registration portion (163) is in the form of a groove or slot analogous to first registration portion (155) of the first positioning component (150). It should be noted that the registration portions of first and second positioning components may be the same as, or different from, each other. For example, one positioning component may have a registration portion configured as a slot, whereas a second positioning component in the same system may have a registration portion configured as a socket, or the like. Second positioning component (151) includes set screws (164) in a top portion (165) that are designed to releasably secure a jig blank (not shown) positioned in first registration portion (163). As described above with reference to the first positioning component, the one or more registration portions on the second positioning component may have any suitable configuration to receive, align, and secure a jig blank during manipulation and machining.

As indicated above, the arthroplasty systems described here are designed to be used with particular arthroplasty jig blanks. The arthroplasty jig blanks generally include an arthroplasty jig blank body and an arm fixture component that is integral with, or configured to be coupled to, the jig blank body. The arm fixture component is configured to couple to the first positioning component in such a way as to position the jig blank body for machining by the machining device. In some variations, arthroplasty jig blanks may be used that are suitable for use in forming multiple different types of arthroplasty jigs. For example, a single arthroplasty jig blank may be used to form either a knee arthroplasty jig or a hip arthroplasty jig.

Figure 2A:
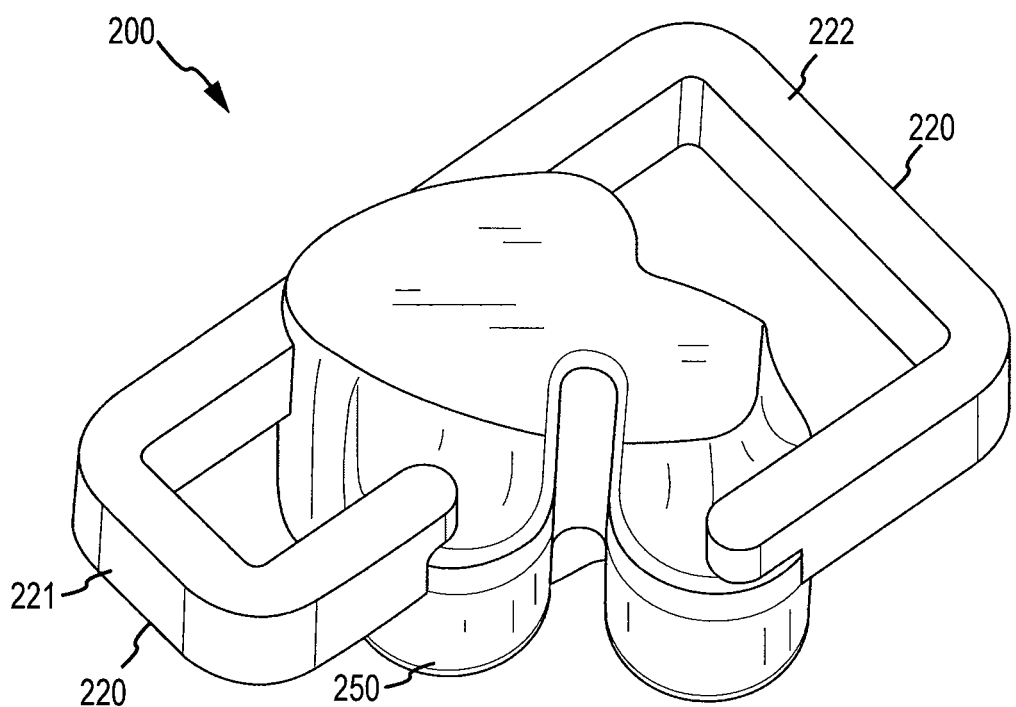
FIG. 2A is a top perspective view of a variation of a right tibial arthroplasty jig blank.
Figure 2B:
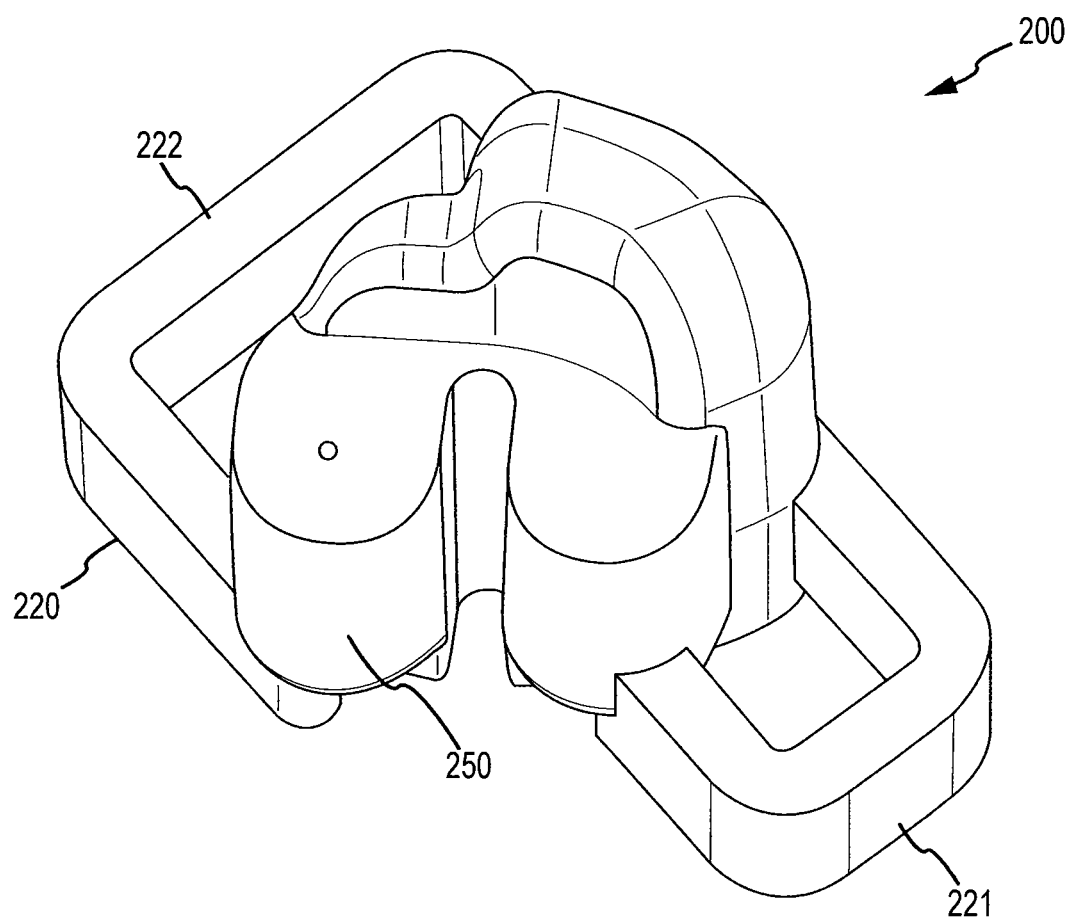
FIG. 2B is a bottom perspective view of the arthroplasty jig blank shown in FIG. 2A.

As a first illustrative variation, FIGS. 2A and 2B show an arthroplasty jig blank for use in making a right tibial arthroplasty jig. The jig blank (200) comprises a jig blank body (250) and an arm fixture component (220). Jig blank body (250) may be selected to have a shape, size, surface, and/or feature of the final desired arthroplasty jig, or that is close to that of the final desired arthroplasty jig. This may, for example, lead to reduced machining time, and/or to enhanced fit with a subject's anatomy. As an example, some variations of near-shape arthroplasty jig blanks are described in U.S. patent application Ser. No. 11/656,363, which has previously been incorporated herein by reference in its entirety. There, near-shape arthroplasty jig blanks are described that have one feature specific to a target anatomy site to be matched by the arthroplasty jig. In the variation shown in FIGS. 2A and 2B, arm fixture component (220) comprises a first U-shaped member (221) and a second U-shaped member (222), with the second U-shaped member extending 180° opposed from the first U-shaped member.

Figure 3A:
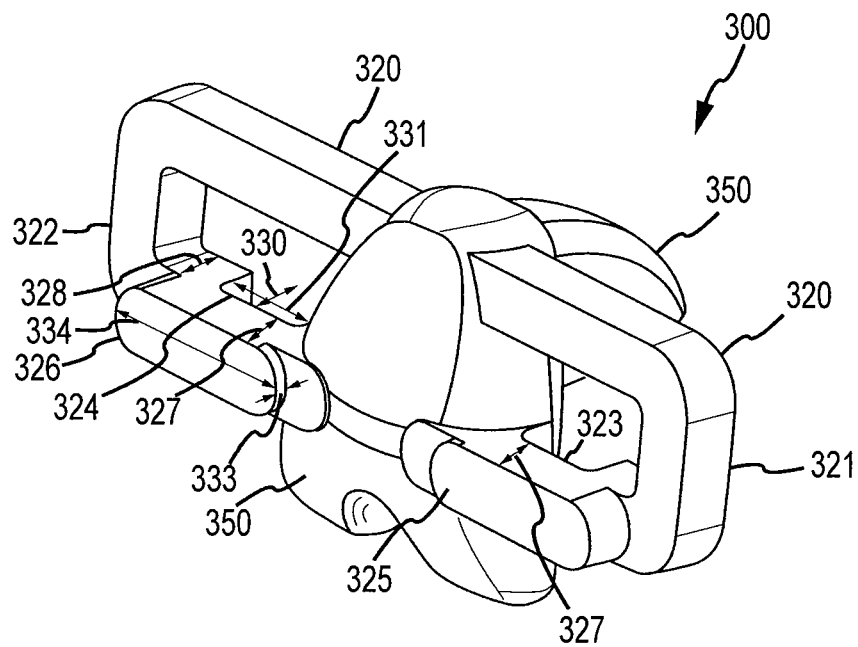
FIG. 3A is a front perspective view of a variation of a left femoral arthroplasty jig blank.
Figure 3B:
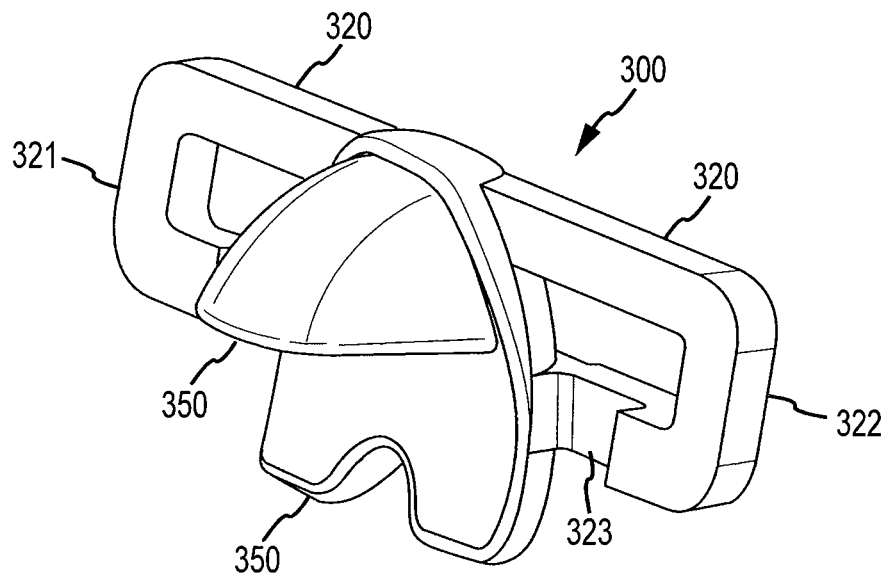
FIG. 3B is a rear perspective view of the arthroplasty jig blank shown in FIG. 3A.

As another illustrative variation, FIGS. 3A and 3B show an arthroplasty jig blank (300) for use in making a left femoral arthroplasty jig. As shown there, jig blank (300) comprises a jig blank body (350) and an arm fixture component (320). Again, the arm fixture component comprises a first U-shaped member (321) and a second U-shaped member (322) extending 180° opposed from the first U-shaped member. The arthroplasty jig blank shown in FIGS. 3A and 3B has a first recessed region (323) and a first protrusion (325) in the first U-shaped member (321) of arm fixture component (320), and a second recessed region (324) and a second protrusion (326) in second U-shaped member (322). The recessed regions (323) and (324) may, for example, allow improved machine tool access to certain portions of jig blank body (350). The recessed regions (323) and (324) may have any appropriate depth and width, such as depth (330) and width (331) of recessed region (324). For example, one or both of the recessed regions may have a depth that is similar to a thickness (e.g., 328) of the arm fixture component (e.g., about 10 mm). In other variations, one or both of the recessed regions may have a depth that is less than a thickness of the arm fixture component. The width of one or both of the recessed regions may be selected to allow desired access to jig blank body (350). For example, one or both of the recessed regions may have a width of about 1 cm to about 2 cm.

Protrusions (325) and (326) may provide improved support in arm fixture component (320) by adding to the arm fixture component thickness near or at the location of one or both recessed regions. For example, in some variations, protrusion (326) may have a depth (333) such that the arm fixture component thickness (327) near or at recessed region (324) may be approximately the same as the arm fixture component thickness (328) beyond recessed region (324). Protrusions may have depths and widths sufficient to reinforce the arm fixture component. For example, protrusion depths may be about 0.5 mm to about 3 mm, and/or protrusion widths may be about 1 cm to about 4 cm.

Some variations of arm fixture components may have recessed regions without corresponding protrusions. Other variations of arm fixture components may have protrusions to strengthen certain portions of the arm fixture component even without the presence of recessed regions. Although recessed regions and protrusions have been shown being used in an arm fixture component having U-shaped members in this example, recessed regions and strengthening protrusions may be used with any suitable configuration of arm fixture component. Further, although the example shown in FIGS. 3A and 3B has two recessed regions (323) and (324) and two protrusions (325) and (326) positioned on opposite sides of jig blank body (350), variations may be used that have only a single recessed region and/or a single protrusion or that have more than two recessed regions and/or protrusions.

As with the tibial jig blank, the femoral jig blank body (350) may be selected to have a shape, size, surface, and/or feature of the final desired arthroplasty jig or that is close to that of the final desired femoral arthroplasty jig to reduce machining time and/or provide an enhanced fit with a subject's anatomy.

Figure 4A:
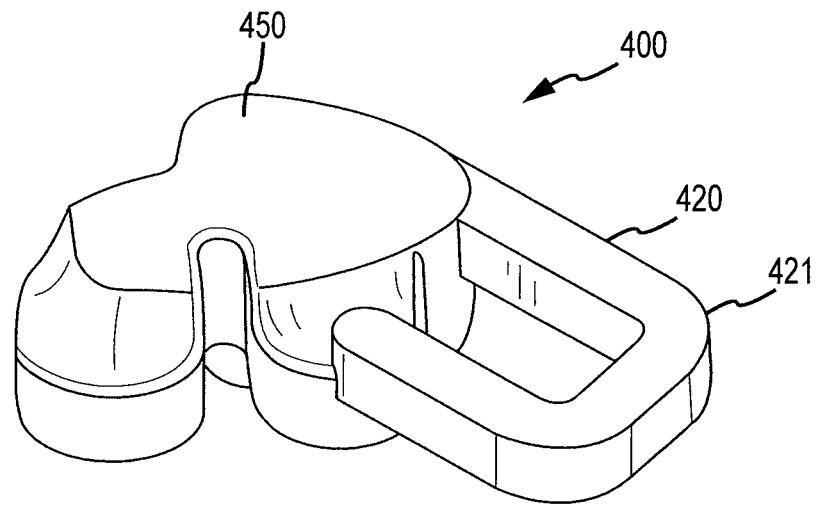
FIGS. 4A and 4B illustrate another variation of a left tibial arthroplasty jig blank.
Figure 4B:
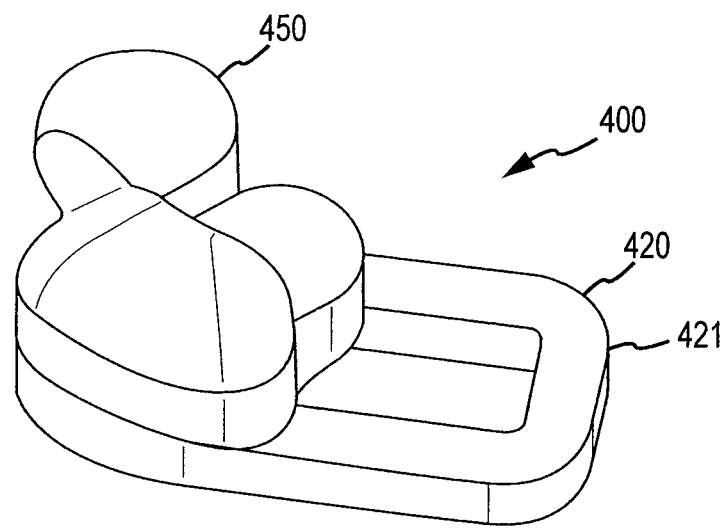
Figure 5A:
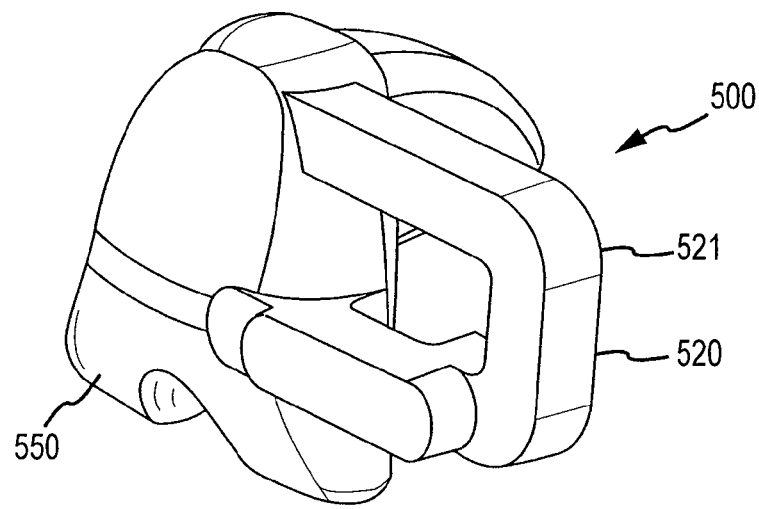
FIGS. 5A and 5B illustrate another variation of a left femoral arthroplasty jig blank.
Figure 5B:
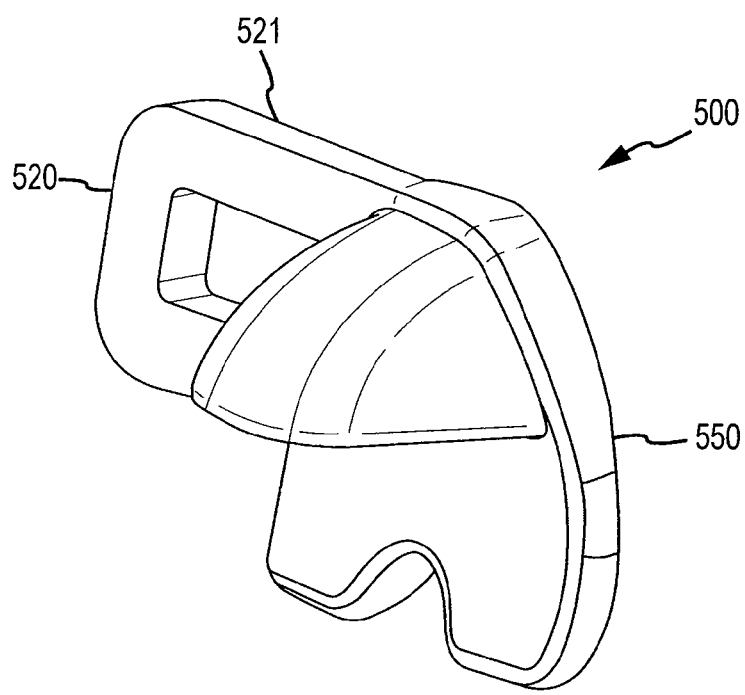

Other variations of arthroplasty jig blanks are illustrated in FIGS. 4A-4B and 5A-5B. FIGS. 4A and 4B show a tibial jig blank (400) having a jig blank body (450) and an arm fixture component (420). Arm fixture component (420) has only a single U-shaped member (421) coupled to, or integral with, jig blank body (450). FIGS. 5A and 5B show a femoral jig blank (500) comprising a jig blank body (550) and an arm fixture component (520). Arm fixture component (520) has only a single U-shaped member (521) coupled to, or integral with, jig blank body (550). Other variations of arthroplasty jigs having different configurations of arm fixture components may also be used, as appropriate.

Generally, in the systems described here, the arm fixture components are configured to be coupled to the first positioning components in such a way as to preserve at least one axis of the coordinate system of the machining device. This allows the same axis in the same coordinate system to be used while machining the jig blank. In some variations of the systems, at least two axes of the coordinate system of the machining device (e.g., two translational axes, or one rotational axis and one translational axis) are preserved when the arm fixture component of the jig blank is coupled to the first positioning component. In still other variations, at least three axes of the coordinate system of the machining device (e.g., two translational axes and a rotational axis) are preserved when coupling the jig blank arm fixture component to the first positioning component. In some cases, at least four axes of the machine device coordinate system (e.g., three translational axes and a rotational axis) are preserved upon coupling the arm fixture component to the first positioning component. By utilizing the same reference frame for both the machining device and the arthroplasty jig blank, machining instructions in the machining device's coordinate system or machining instructions in an arthroplasty jig blank coordinate system can be used. This may simplify the process for creating machining instructions. It also may reduce the need to verify the position of the jig blank during the machining process, and reduce the likelihood of translation errors occurring when converting from one coordinate system to another.

To preserve one or more axes of the machining device's coordinate system, and transfer this frame of reference to the jig blank for machining, the arm fixture component and the positioning component may be coupled to each other in a particular way. As an example, a registration portion of the positioning component can align and position the arm fixture component of the jig blank so that the jig blank body can be moved and machined along or about the one or more axes of the machine coordinate system, to allow machining of at least a portion of the jig blank body.

Figure 6A:
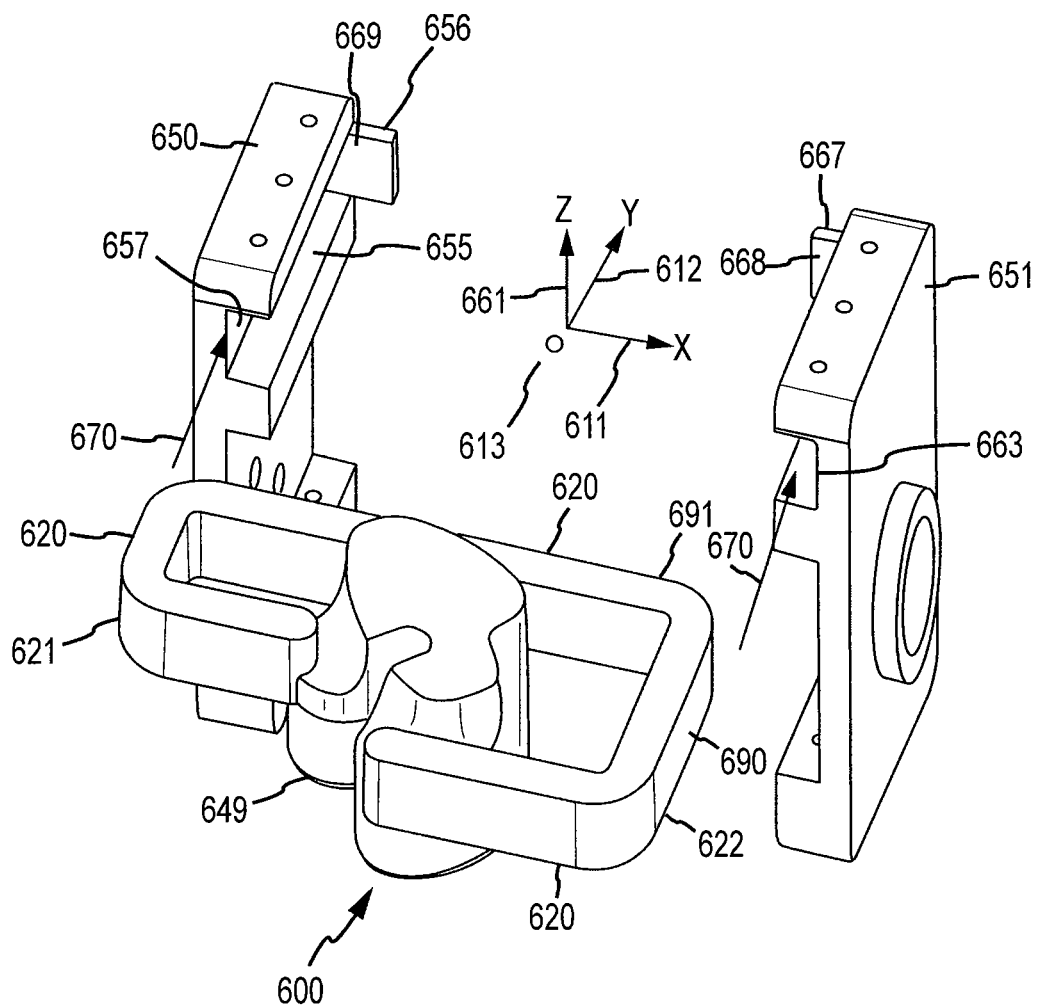
FIG. 6A illustrates a pair of positioning components, and an arthroplasty jig blank that can be coupled to the pair of positioning components.
Figure 6B:
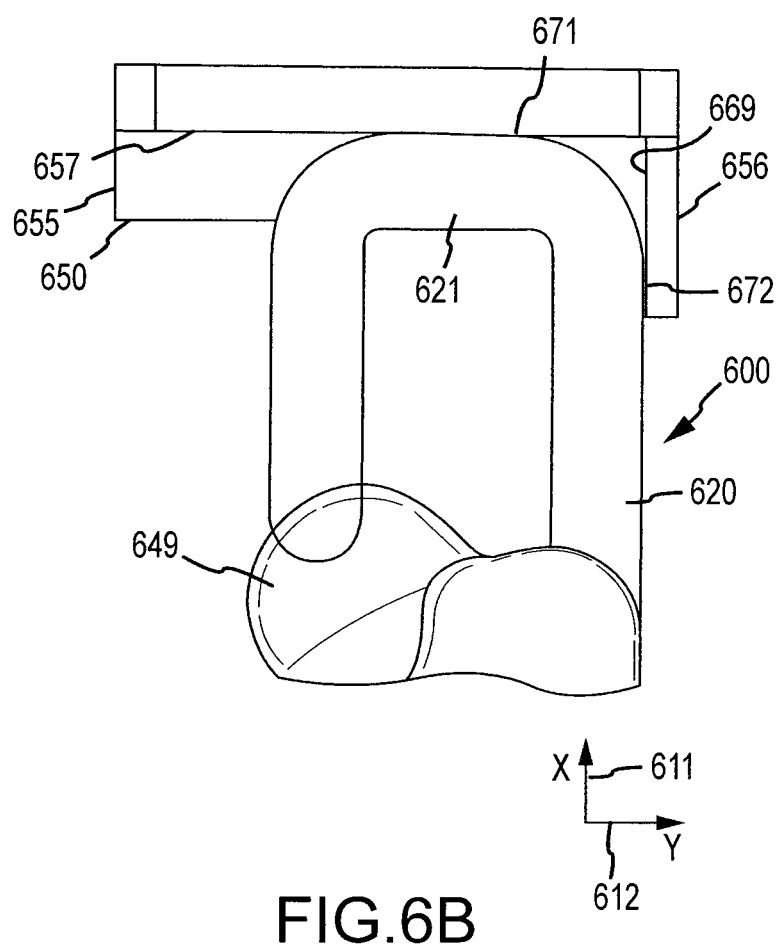
FIG. 6B shows an alternate view of a portion of an arthroplasty jig blank being coupled to a positioning component.
Figure 6C:
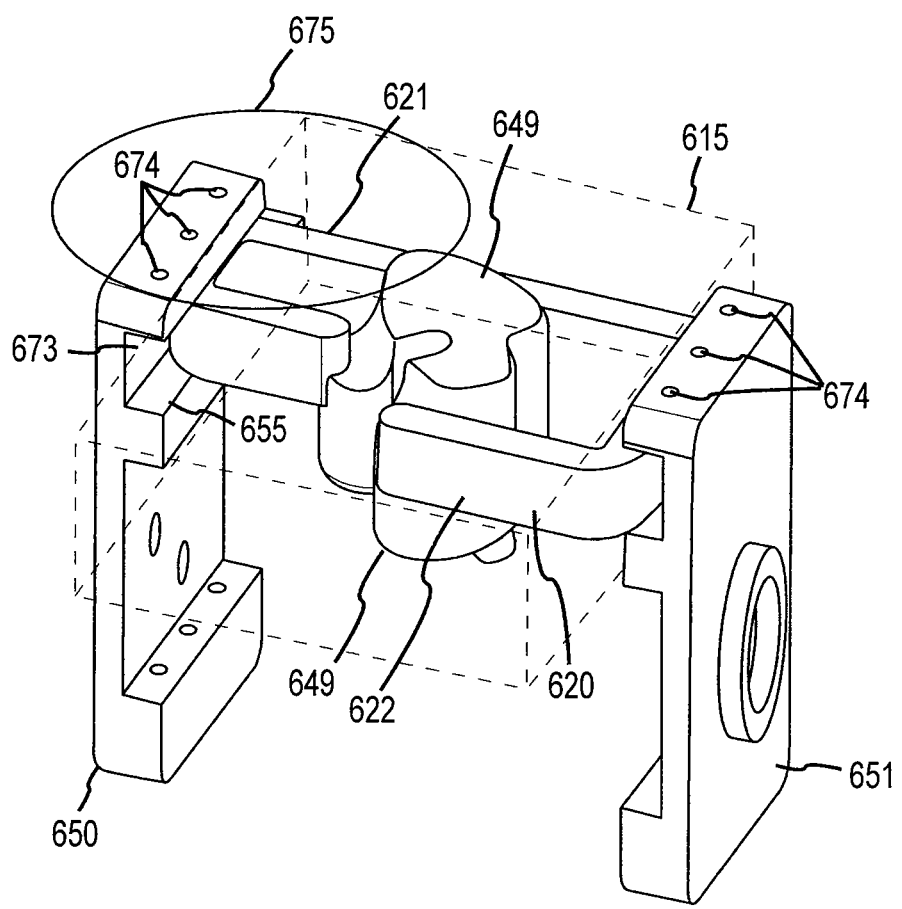
FIG. 6C shows an arthroplasty jig blank that has been coupled to a pair of positioning components.

FIGS. 6A, 6B, and 6C illustrate an example of a method of mounting an arthroplasty jig blank (600) into a first positioning component (650) and a second positioning component (651). Arthroplasty jig blank (600) comprises an arm fixture component (620) and a jig blank body (649). In this variation, arm fixture component (620) has a first U-shaped member (621) and a second U-shaped member (622). First positioning component (650) has a first registration portion (655) in the form of a slot or groove having a surface (657) that can be aligned with the Y-axis (612) of a machining device (not shown). In this variation, first positioning component (650) also has a second registration portion (656) in the form of a stop having a surface (669) that can be aligned with the X-axis (611) of the machining device. Second positioning component (651) has a first registration portion (663) in the form of a slot having a surface that can also be aligned with the Y-axis, and a second registration portion (667) in the form of a stop having a surface (668) that can be aligned with the X-axis. In this variation, as arrows (670) indicate, arm fixture component (620) of jig blank (600) is configured to slidably engage with first registration portion (655) of first positioning component (650) to abut second registration portion (656), and to slidably engage with first registration portion (663) of the second positioning component (651) and abut second registration portion (667). By doing so, jig blank body (649) can be aligned with two translational axes (e.g., X- and Y-axes) of the machining device.

Further, an origin (613) of one or more of the translational axes of the machining device (e.g. the X-axis (611), Y-axis (612), and Z-axis (661)) can be set when the jig blank is mounted into a positioning component and aligned with the use of one or more registration portions of the positioning component. For the variation shown in FIGS. 6A-6C, the origin can be set when the arm fixture component is inserted into registration portions (655) and (663) to align with the Y-axis, and abuts registration portions (656) and (667) to align with the X-axis. Thus, the origin used in machine files that are input into the machining device to deliver cutting, milling, and drilling instructions can be made to correspond to the origin of a jig blank body so positioned in the machining device.

To preserve and transfer the machining device's coordinate system from the positioning component to the jig blank, the arm fixture component to be coupled to the positioning component has one or more surfaces configured to align with the one or more registration portions of the positioning component. Thus, as illustrated in FIGS. 6A and 6B, arm fixture component (620) of jig blank (600) has first U-shaped member (621) having a first planar surface (671) configured to align with a first planar surface (657) of first registration portion (655) of first positioning component (650). First planar surface (657) of the first registration portion (655) is aligned with the Y-axis (612) of the machining device. First U-shaped member (621) also has a second planar surface (672) that is configured to align with a second planar surface (669) of the first positioning component's second registration portion (656). Second planar surface (669) is in turn aligned with the X-axis (611) of the machining device. Similarly, second U-shaped member (622) of arm fixture component (620) has a planar surface (690) configured to be aligned with a planar surface of the second positioning component's first registration portion (663). Planar surface (690) is in turn aligned with the Y-axis (612) of the machining device. Second U-shaped member (622) has another planar surface (691) configured to be aligned with surface (668) of the second positioning component's second registration portion (667), where surface (668) is aligned with the X-axis (611) of the machining device.

Therefore, and as illustrated in FIG. 6C, when arm fixture component (620) is slidably engaged into first registration portions (655) and (663) of the first and second positioning components (650) and (651), respectively, to abut surfaces (669) and (668) of second registration portions (656) and (667), respectively, and secured (e.g., with set screws (674) shown in the encircled region (675)), at least a portion of jig blank body (649) can be machined. As indicated approximately by the volume (615), a significant volume of jig blank body (649) can be accessed by one or more machining tools of the machining device.

As described here, the volume of the jig blank body that can be accessed by one or more machining tools in this way may also be referred to as a "workable volume" of the jig blank body. In some variations, systems described here may allow about at least about 10 cubic inches, at least about 15 cubic inches, at least about 20 cubic inches, at least about 25 cubic inches, at least about 30 cubic inches, at least about 35 cubic inches, at least about 40 cubic inches, at least about 45 cubic inches, at least about 50 cubic inches, at least about 55 cubic inches, or at least about 60 cubic inches of workable volume on the jig blank. Positioning components (650) and (651) can be rotated 360° about rotational axis ω of the machining device to allow access to the workable volume from multiple angles.

Figure 7:
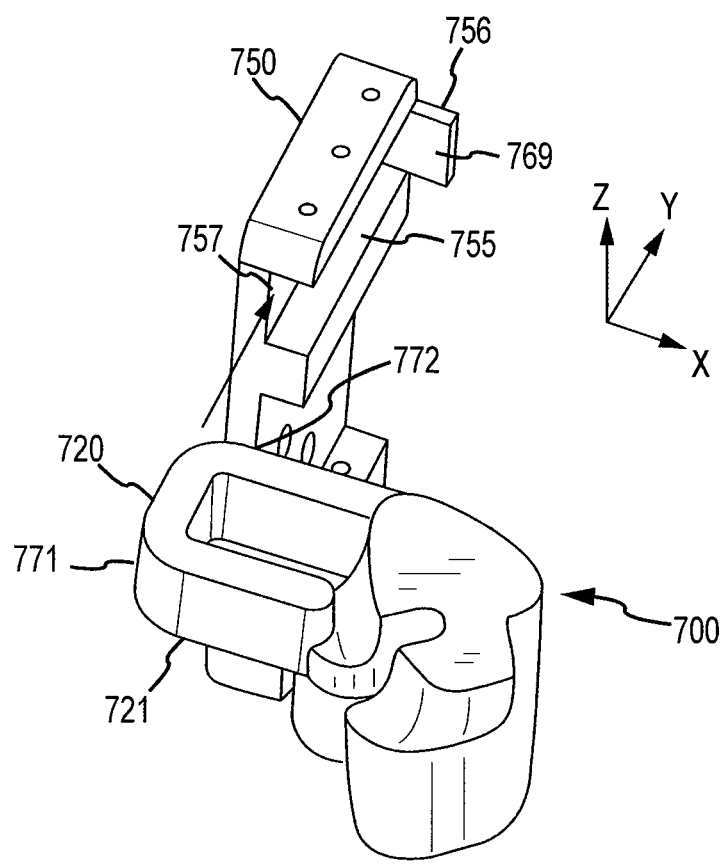
FIG. 7 shows a single positioning component and a variation of an arthroplasty jig blank that can be coupled to the single positioning component.

In other variations of the systems, only one positioning component may be used to receive, align, and secure a jig blank body while machining. An example of such a variation is shown in FIG. 7. There, a first positioning component (750) has a first registration portion (755) in the form of a slot having a planar surface (757) that can be aligned with the Y-axis of a machining device (not shown). First positioning component (750) also has a second registration portion (756)

having a planar surface (769) that can be aligned with the X-axis of the machining device. An arthroplasty jig blank (700) has an arm fixture component (720) having a single U-shaped member (721). U-shaped member (721) has a first planar surface (771) that can be aligned with surface (757) of a first registration portion (755) to align with the Y-axis of the machining device. U-shaped member (721) also has a second orthogonal planar surface (772) that can be aligned with surface (769) of second registration portion (756) to align with the Y-axis of the machining device.

By using only one positioning component, it may be possible to increase accessible volume of the jig blank body for machining. In addition, systems using only one positioning component may be configured to couple with arm fixture components extending from only one side of a jig blank body (e.g., a single U-shaped member instead of two, opposed U-shaped members). This may, for example, result in relatively easy removal of the arm fixture component from the jig blank to form a final arthroplasty jig. As a result, machining time to remove the arm fixture component from only one side of the jig blank may be reduced.

In the systems described here, the arm fixture components of the arthroplasty jig blanks may have any suitable configuration to position the jig blank body into a machining device (e.g., to preserve one or more axes of the machining device's coordinate system), and/or to stabilize the jig blank body from the force and torque it can experience during machining. For example, a spindle unit rotating at about 12,000 rpm can generate between about 5 to about 15 pounds of vertical force. Thus, it may be desirable for an arm fixture component to be able to provide support along multiple axes to cause minimal deformations and movements (e.g., of less than about 0.1 mm, or less than about 0.08 mm, or less than about 0.06 mm, or less than about 0.04 mm, or even less than about 0.02 mm). Providing such support may aid in the accurate machining of any feature, especially detailed features that have small dimensions (e.g., less than about 2 mm, or less than about 1 mm, or less than about 0.5 mm, or even smaller). In addition, arm fixture components typically are removed from the jig blank body when machining is complete to form the final customized arthroplasty jig. Therefore, to reduce the time for removal of the arm fixture component (e.g., by machining), it may be desired to reduce the area of contact between the jig blank body and the arm fixture component.

Different variations of arm fixture component designs other than those shown above may be used in combination with a positioning component such as that shown in FIGS. 1A and 1B to align, position and support a jig blank body along one or more axes of a machining device. For example, arm fixture components can include other features, such as drilling holes or slots that can increase machine tool access to the jig blank body. Some illustrative, non-limiting examples of arm fixture components are provided in FIGS. 8A-8E.

Figure 8A:
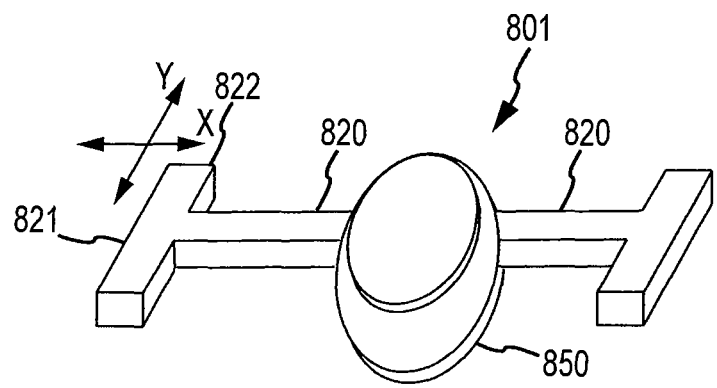
FIGS. 8A-8E depict various configurations of arthroplasty jig blanks having different arm fixture component designs.
Figure 8B:
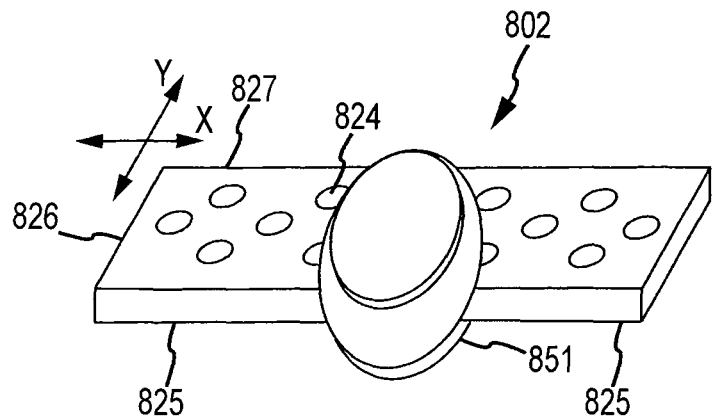
Figure 8C:
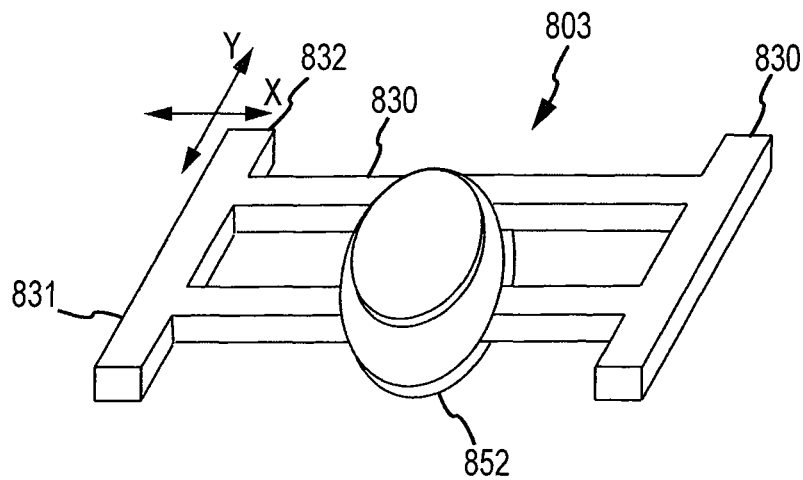
Figure 8D:
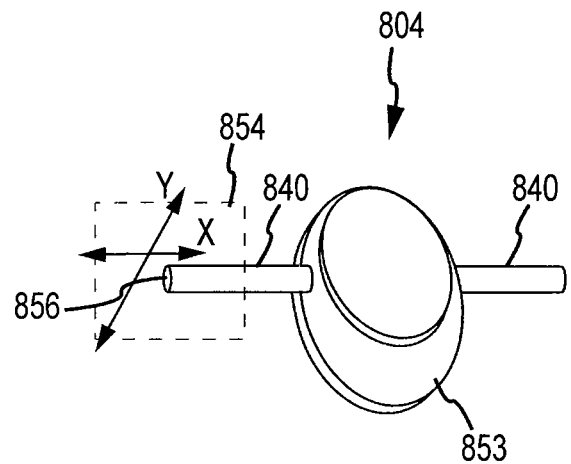
Figure 8E:
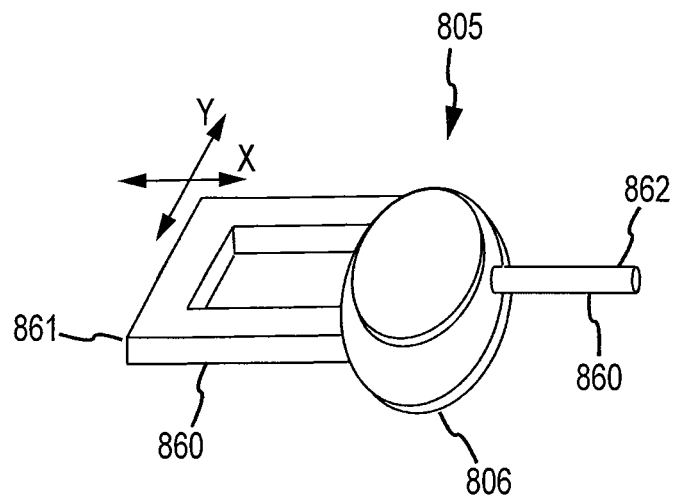

FIG. 8A shows a jig blank (801) having a T-shaped arm fixture component (820) integral with, or coupled to, a jig blank body (850). Arm fixture component (820) has a first planar surface (821) that can be parallel to a Y-axis of a machining device, and a second orthogonal planar surface (822) that can be parallel to an X-axis of a machining device. FIG. 8B shows a jig blank (802) having a rectangular-shaped arm fixture component (825) that is integral with, or coupled to, a jig blank body (851). Arm fixture component (825) has two orthogonal planar surfaces (826) and (827) that can be parallel to Y- and X-axes of a machining device, respectively. The rectangular-shaped arm fixture component can include one or more perforations (824) to reduce bulk, and to decrease contact area between the jig blank body and the arm fixture component, thereby facilitating removal of the arm fixture component. FIG. 8C shows a jig blank (803) having a π-shaped arm fixture component (830) that is integral with, or coupled to, a jig blank body (852). Again, π-shaped arm fixture component (830) has a first planar surface (831) and a second orthogonal planar surface (832) that can be aligned with Y- and X-axes, respectively, of the machining device. FIG. 8D shows a jig blank (804) having a rod-like arm fixture component (840) that is integral with, or coupled to, jig blank body (853). Rod-like arm fixture component (840) has a planar face (856) that is orthogonal to a plane (854) that is tangent to a curved side of the arm fixture component. Thus, planar face (856) can be aligned with a Y-axis of the machining device, and tangent plane (854) can be aligned with an X-axis of the machining device.

Of course, and as shown in FIGS. 2A-2B and 3A-3B, the arm fixture component need not be symmetrical from side to side, top to bottom, and/or front to back. Therefore, any combination of arm fixture components may be used in a single jig blank. For example, in FIG. 8E, a jig blank (805) is illustrated that has an arm fixture component (860) having a U-shaped member (861) extending from one side of the jig blank body (806) and a rod-like member (862) extending from the opposite side of the jig blank body (806). Any other suitable configurations may also be used.

Figure 9A:
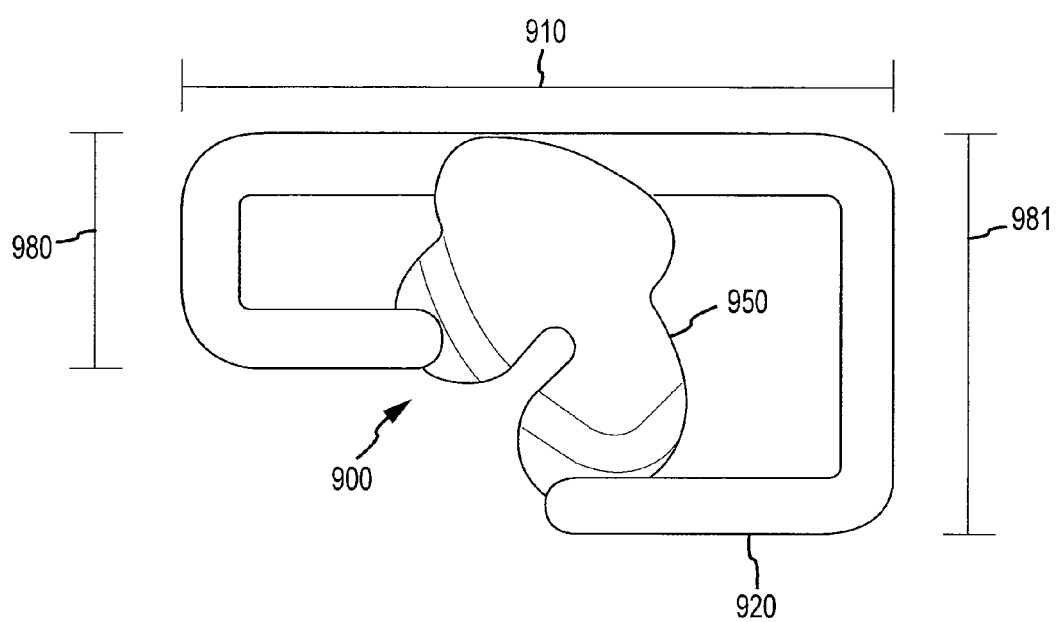
FIG. 9A is a top view of a variation of an arthroplasty jig blank.
Figure 9B:
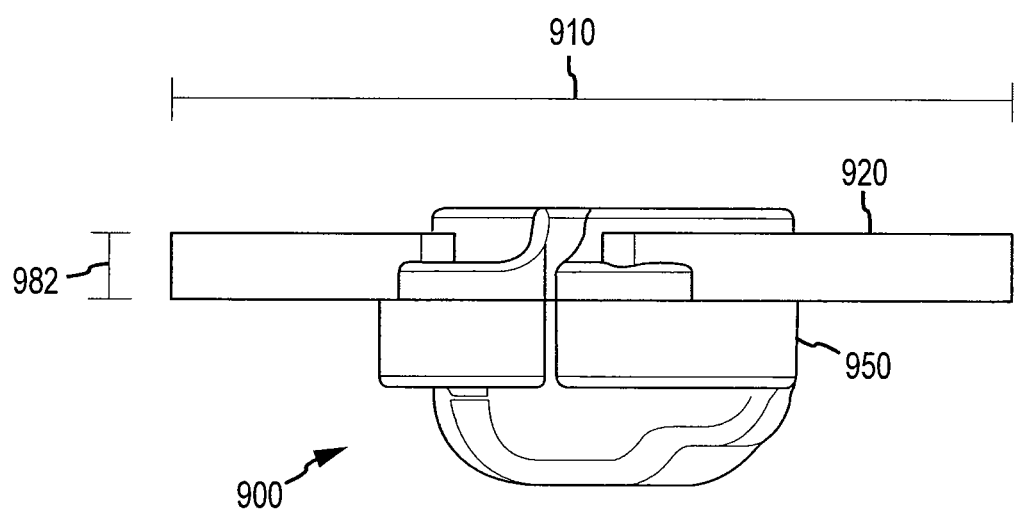
FIG. 9B is a rear side view of the arthroplasty jig blank of FIG. 9A.

The dimensions of the arm fixture component on an arthroplasty jig blank may be selected based on the type and/or size of the arthroplasty jig involved, and/or the material used, and/or the dimensions of the corresponding positioning component. FIGS. 9A and 9B show a tibial jig blank having a jig blank body (950) and an arm fixture component (920). A length-wise cross-sectional dimension (910) of arm fixture component (920), which allows jig blank (900) to be connected between two positioning components (not shown), may in part determine the workable volume of jig blank body (950). In some variations, jig blanks can be provided that have a length-wise cross-sectional dimension of about 4 inches to about 8 inches (e.g., about 4 inches, about 5 inches, about 6 inches, about 7 inches, or about 8 inches). In some cases, the length-wise cross-sectional dimension can be even smaller (e.g., about 3 inches), or larger (e.g., about 9 inches or 10 inches). A longer length-wise dimension is suitable for use with relatively spaced-apart positioning components. While the longer lever arm may decrease the jig blank's ability to withstand force or torque during machining, it may also increase the volume accessible by one or more machining tools. A widthwise cross-sectional dimension of the arm fixture component of the jig blank (e.g., dimensions (980) and (981) in FIG. 9A) can in part determine the jig blank's ability to resist non-normal force or torque while machining. In certain variations, jig blanks may be used that have an arm fixture component having a widthwise cross-sectional dimension (980) or (981) of about 1 inch to about 6 inches (e.g., about 1 inch, about 2 inches, about 3 inches, about 4 inches, about 5 inches, or about 6 inches).

The arm fixture component may have any suitable thickness (dimension (982) in FIG. 9B), again based on the type and/or size of arthroplasty jig being manufactured, and/or the material used, and/or the corresponding positioning component used with the arthroplasty jig blank. A thicker arm fixture component may be better able to stabilize the jig blank against movement, bending, and/or deformation caused by force and/or torque from the machining process. However, a thicker arm fixture component may also take longer to remove from the jig blank body. In some variations, jig blanks having arm fixture components with thicknesses of about 10 mm to about 20 mm (e.g., about 12 mm, about 14 mm, about 16 mm, or about 18 mm) may be used. In some cases, thicknesses of less than 10 mm (e.g., about 8 mm), or more than 20 mm (e.g., about 22 mm), may be used. Of course, the dimensions used for the arm fixture component may depend on the material used. For example, a stiffer material may require less thickness to provide the necessary level of stability and deformation resistance than a compliant material. As an example, an arthroplasty jig blank made from Delrin™ polymer having an arm fixture component with a configuration similar to that shown in FIGS. 2A and 2B or 3A and 3B, a thickness of about 10 mm to about 20 mm, and length-wise cross-sectional dimension of about 4 inches to about 8 inches, is expected to exhibit acceptable stability and deformation resistance under typical machining forces (e.g., about 5 to about 15 pounds of vertical force).

Any suitable material may used to form the arthroplasty jig blanks. For example, biocompatible polymers may be used as they may be relatively easy to machine. Examples of biocompatible polymers that can be used include as acetal resins, e.g., Delrin™, Nylon™, polycarbonates, polyetheretherketones (PEEK), polyethylenes, polypropylenes, Teflon™, polystyrenes, polyacrylates, polyamides, polyesters, polyurethanes, vinyl polymers, and combinations or blends thereof may be used. In other situations, an easily machineable biocompatible metal may be used to form the jig blanks, such as aluminum. More than one material may be used in an arthroplasty jig, e.g., the arm fixture component may be formed from a different polymer from the jig body.

Methods for manufacturing an arthroplasty jig by machining are also provided. The methods can incorporate the use of automated machining devices, such as CNC machines, to rapidly and accurately machine a custom arthroplasty jig. The methods can be used to make any type of arthroplasty jig, such as a knee arthroplasty jig (tibia or femur), a hip arthroplasty jig, an elbow arthroplasty jig, or a spinal arthroplasty jig.

The methods include coupling an arm fixture component of an arthroplasty jig blank to a first positioning component that is coupled to, or integral with, a machining device. The first positioning component is adjusted to position a jig blank body of the arthroplasty jig along or about one or more axes of the machining devices. In many cases, the machining device is a CNC machine, and the positioning component is adjusted automatically by instructions input into the CNC machine. The instructions may be used to position the jig blank body using one or more axes of the coordinate system of the machining device. For example, the first positioning component can be rotated 360° about a first rotational axis of the machining device to facilitate machine tool access to the body of the jig blank.

The methods include machining at least a portion of the jig blank body with one or more machining tools of the machining device to form the arthroplasty jig. After the surfaces of the arthroplasty jig blank body have been machined as desired, the arm fixture component can be removed from the jig blank body (e.g., by cutting the arm fixture component off with a milling tool or other cutting tool). Some methods can include coupling the arm fixture component of the arthroplasty jig blank to a second positioning component that is coupled to, or integral with, the machining device. Any suitable commercially available software may be used to provide instructions to the machining device, e.g., Visualmill, available from Mecsoft Corp. Irvine, Calif. (www.mecsoft.com), SolidCAM, available from www.solidcam.de, Camworks™, available from Geometric Technologies, Scottsdale, Ariz., www.teksoft.com, AutoCAM, available from Compass Solutions, Ltd., www.compasssolutions.co.uk/AutoCAM/html, and others.

Figure 10:
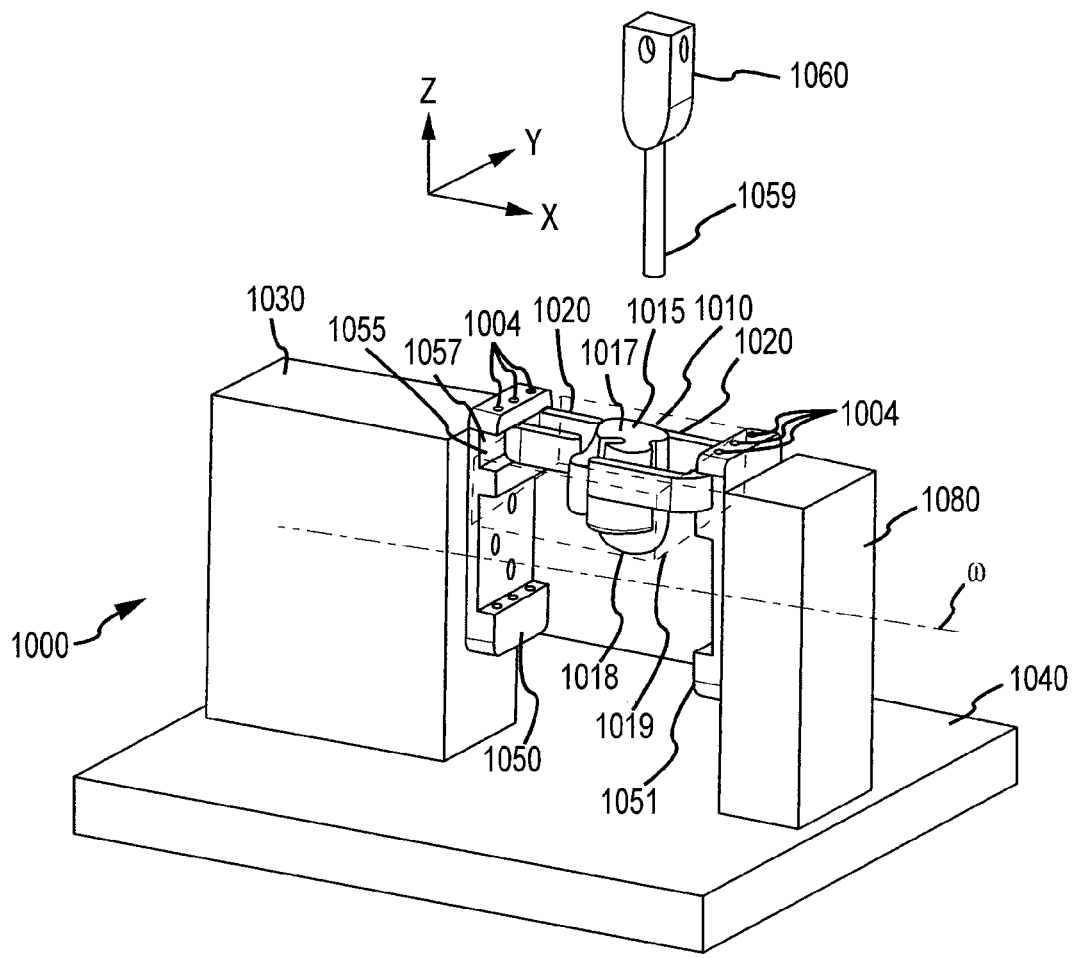
FIG. 10 schematically illustrates a variation of a method of machining an arthroplasty jig blank to form an arthroplasty jig.

A variation of a method of machining an arthroplasty jig is illustrated in FIG. 10. FIG. 10 shows a first positioning component (1050) coupled to a rotary driver unit (1030) of a CNC machine (1000) mounted on an X-Y table (1040), such that the first positioning component can rotate around the machining device's first rotational axis ω. An arthroplasty jig blank (1010) is coupled to first positioning component (1050) via an arm fixture component (1020).

Arm fixture component (1020) is mounted into first positioning component (1050) in such a manner as to align the jig blank body with first and/or or second translational axes of CNC machine (1000). As a result, those axes of the machining device can be used to machine the jig blank body without need for coordinate transformation. Thus, the method can simplify the process of creating and delivering instructions for the machining of the jig blank. For example, the arm fixture component can be aligned with a first translational axis of CNC machine (1000) by aligning a face (not shown) of the arm fixture component (1020) with a face (1057) of a first registration portion (1055) of a first positioning component (1050) that is aligned with the Y-axis. Arm fixture component (1020) can be aligned with a second translational axis of CNC machine (1000) by providing a face of a second registration portion (not shown) that is orthogonal to face (1057) of the first registration portion and aligned with the X-axis of CNC machine (1000). Once the arm fixture component is coupled to the first positioning component so that the jig blank body is aligned with one or more axes of CNC machine (1000), it can be secured in place in the positioning component (e.g., by using set screws (1004) or a clamp). Thus, jig blank (1010) and, therefore, jig blank body (1015), are aligned with the first rotational axis ω, the first translational axis X, and the second translational axis Y of CNC machine (1000).

Optionally, the methods can include coupling the arm fixture component (1020) to a second positioning component (1051) that is in turn coupled to a stabilizing unit (1080) of CNC machine (1000). Coupling the arm fixture component between a first and a second positioning component may provide increased stability during movement of the jig blank, and especially during machining of the jig blank as the jig blank is rotated about rotational axis ω.

After the jig blank is securely mounted into one or more positioning components coupled to CNC machine (1000) so that jig blank is aligned with one or more axes of CNC machine (1000), the methods include applying one or more machining tools to the jig blank body to form a custom arthroplasty jig. Referring again to FIG. 10, a spindle unit (1060) comprising an interchangeable cutting, milling, or drilling tool (1059) can be translated along the Z-axis, (e.g., raised and lowered), to access and machine the jig blank body (1015). The spindle unit can also be translated along the X- and Y-axes to machine jig blank body (1015). The positioning component or components can rotate a full 360° about the rotational axis ω of CNC machine (1000), so that various surfaces, including a top surface (1017) and a bottom surface (1018) of the jig blank body (1015), can be machined and accessed. Thus, a workable volume (1019) can be accessed at a variety of angles as the positioning component or components are rotated about rotational axis ω.

By using a CNC machine in the methods described here to automatically machine the arthroplasty jig blanks, the machining time for a custom arthroplasty jig may be reduced from about 2-3 hours to about 20 minutes or less. In addition, the use of arthroplasty jig blanks having jig blank bodies that have a size, shape, surface, and/or feature of the final desired jig or that are close to that of the final desired jig, for example the near-shape jig blanks described in U.S. patent application Ser. No. 11/656,323, which has already been incorporated by reference in its entirety, may reduce machining time further.

Figure 11A:
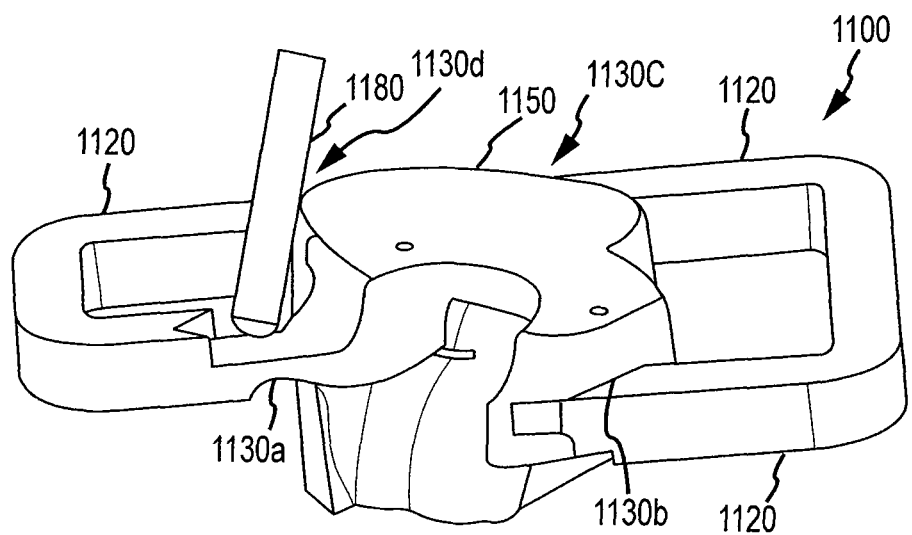
FIGS. 11A and 11B illustrate an example of a machining step to remove an arm fixture component from a machined arthroplasty jig blank to form an arthroplasty jig.
Figure 11B:
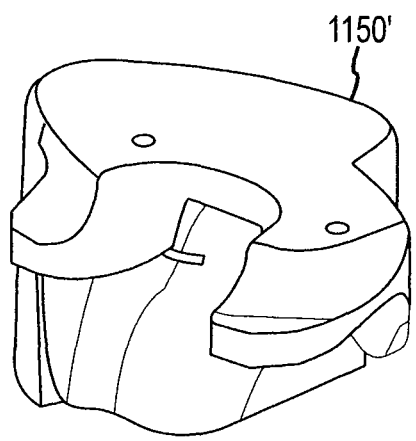

FIGS. 11A and 11B illustrate a variation of a method of removing the arm fixture component from a machined jig blank. As shown there, a machined jig blank (1100) has an arm fixture component (1120) and a jig blank body (1150). A machining tool such as a milling tool is applied to all attachment regions (1130a), (1130b), (1130c), and (1130d) between arm fixture component (1120) and jig blank body (1150) to remove the arm fixture component from the jig blank body, thereby forming the finished custom arthroplasty jig (1150'). Other methods may be used in some cases to remove an arm fixture component from a machined jig blank (e.g., cleaving along a prescored line). After the arm fixture component has been removed, the machined jig blank may undergo further processing (e.g., polishing and/or filing to remove burrs, etc.).

Methods are also provided for making an arthroplasty jig blank. Arthroplasty jig blanks may be formed using, for example, polymer molding or forming techniques, such as injection molding and/or compression molding.

Injection molding includes forming a mold, and injecting the mold with an injectable thermoplastic or thermosetting polymer or polymer blend. If a thermoplastic polymer or polymer blend is used, then the thermoplastic polymer or polymer blend is allowed to cool below its melt. If a thermoset polymer or polymer blend is used, then the thermoset polymer or polymer blend is allowed to cure in the mold. Thereafter, the molded polymer or polymer blend is released from the mold to form an arthroplasty jig blank comprising a jig blank body and an arm fixture component that is integral with, or coupled to, the jig blank body.

Compression molding involves filling an open mold with a thermoplastic or thermoset polymer or polymer blend, closing the mold to apply pressure to force the polymer or polymer blend to fill the mold, and then allowing a thermoplastic to cool below its melt or curing a thermoset polymer or polymer blend in the mold before releasing the mold. In many cases, with either injection molding or compression molding, the arm fixture component and the jig blank body will form a unitary body that is formed in a single mold. However, in some cases, the arm fixture component may be molded and formed separately from the jig blank body, and the two can then be affixed together as a separate step.

Figure 12:
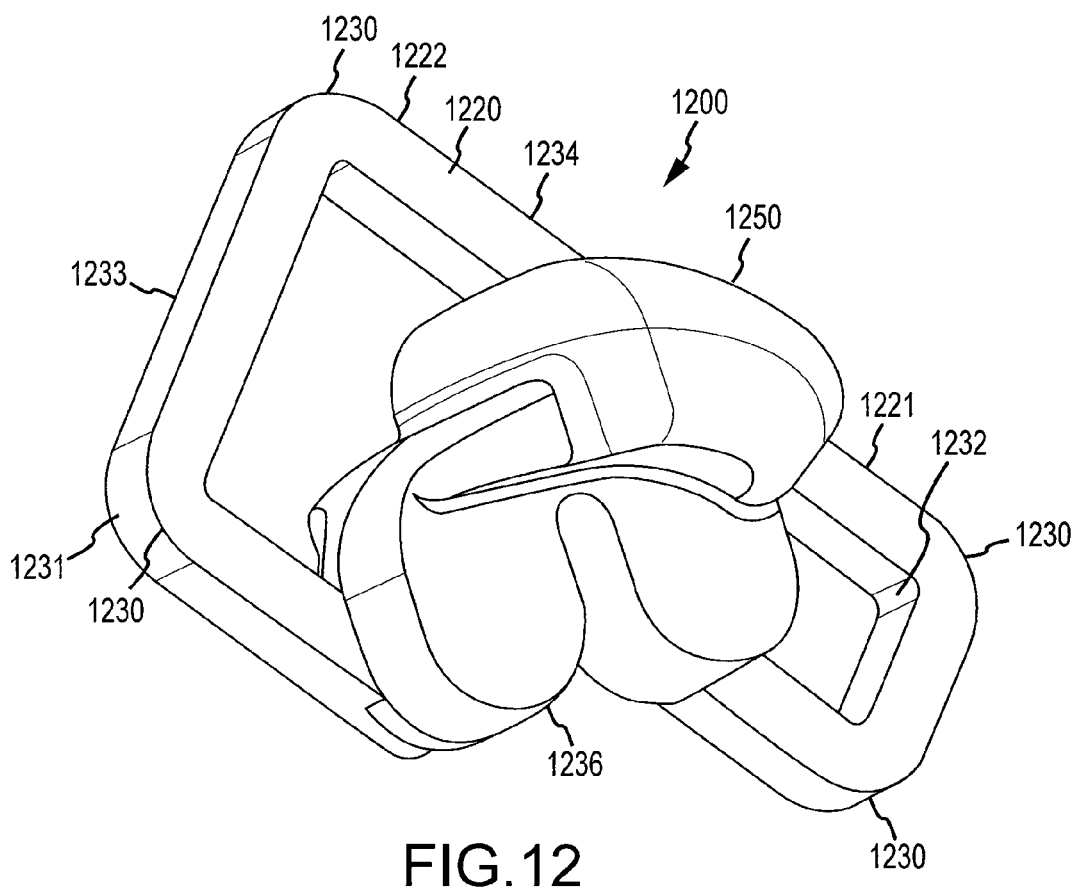
FIG. 12 is a perspective view of a variation of an arthroplasty jig blank.

Because right angles may present difficulties in injection-molded pieces and in polymer molding techniques in general, the arm fixture component may be designed to contain no right angles, or few right angles. For example, and referring now to FIG. 12, the U-shaped members (1221) and (1222) of an arm fixture component (1220) of a jig blank (1200) have corners (1230) including beveled exterior surfaces (1231) and beveled interior surfaces (1232) instead of a right angle. However, the U-shaped members still have two orthogonal, planar surfaces (1233) and (1234) that can be used to align the jig blank with translational axes of the machining device. The jig blank body (1250) also may include beveled edges (1236) to facilitate molding of the jig blanks.

Any suitable polymer may used to mold or form the arthroplasty jig blanks. For example, moldable biocompatible polymers such as acetal resins, e.g., Delrin™, Nylon™, polycarbonates, polyetheretherketones (PEEK), polyethylenes, polypropylenes, Teflon™, polystyrenes, polyacrylates, polyamides, polyesters, polyurethanes, vinyl polymers, and combinations or blends thereof may be used. Additionally, more than one material may be used in forming an arthroplasty jig blank.

While the systems, methods, and devices have been described in some detail here by way of illustration and example, such illustration and example is for purposes of clarity of understanding only. It will be readily apparent to those of ordinary skill in the art in light of the teachings herein that certain changes and modifications may be made thereto without departing from the spirit and scope of the appended claims.

What is claimed is:

1. An arthroplasty jig manufacturing system comprising:
a first positioning component that is integral with, or configured to be coupled to, a machining device; and
an arthroplasty jig blank comprising a jig blank body including at least one feature specific to a target anatomy site and an arm fixture component, wherein the arm fixture component comprises a first U-shaped member extending from the jig blank body,
wherein the arm fixture component is configured to couple to the first positioning component, and wherein coupling the arm fixture component to the first positioning component positions the jig blank body for machining by the machining device.

2. The arthroplasty jig manufacturing system of claim 1, wherein the first positioning component is configured to position the jig blank body along a plane defined by first and second translational axes of the machining device, when the arm fixture component is coupled to the first positioning component.

3. The arthroplasty jig manufacturing system of claim 2, wherein the arm fixture component comprises a first surface and a second surface, and when the arm fixture component is coupled to the first positioning component, the first surface is aligned with one of the first and second translational axes, and the second surface is aligned with the other of the first and second translational axes.

4. The arthroplasty jig manufacturing, system of claim 1, wherein the first positioning component is configured to rotate the jig blank body around a first rotational axis of the machining device, when the arm fixture component is coupled to the first positioning component.

5. The arthroplasty jig manufacturing system of claim 1, further comprising a second positioning component, wherein the arm fixture component is configured to couple to the second positioning component.

6. The arthroplasty jig manufacturing system of claim 1, further comprising a second positioning component, wherein the arm fixture component comprises a second U-shaped member configured to couple to the second positioning component.

7. The arthroplasty jig manufacturing system of claim 1, further comprising a clamp configured to releasably secure the arm fixture component to the first positioning component.

8. The arthroplasty jig manufacturing system of claim 1, wherein when the arm fixture component is coupled to the first positioning component, the first positioning component positions the jig blank body so that a volume of the jig blank body is accessible by one or more machining tools of the machining device.

9. The arthroplasty jig manufacturing system of claim 8, wherein the first positioning component is configured to position the jig blank body so that at least about 30 cubic inches of the jig blank body is accessible by the one or more machining tools of the machining device.

10. The arthroplasty jig manufacturing system of claim 1, wherein the arm fixture component has a dimension of about 4 inches to about 8 inches.

11. The arthroplasty jig manufacturing system of claim 1, wherein the arthroplasty jig blank comprises a knee arthroplasty jig blank.

12. The arthroplasty jig manufacturing system of claim 1 wherein the arthroplasty jig blank comprises a hip arthroplasty jig blank.

13. The arthroplasty jig manufacturing system of claim 1 wherein the arthroplasty jig blank comprises a shoulder arthroplasty jig blank, an elbow arthroplasty jig blank, or a spinal arthroplasty jig blank.

14. A positioning component for positioning a jig blank body of an arthroplasty jig blank in a machining device, the positioning component comprising:
    a positioning component body that is integral with, or configured to be coupled to, the machining device, the positioning component body comprising a first registration portion that is configured to couple with an arm fixture component, wherein the arm fixture component comprises a first U-shaped member extending from the jig blank body,
    wherein coupling the first registration portion of the positioning component body with the arthroplasty jig blank positions the jig blank body along or about one or more axes of the machining device to allow for machining of at least a portion of a jig blank body and wherein the jig blank body includes at least one feature specific to a target anatomy site.

15. The positioning component of claim 14, wherein the first registration portion is configured to be aligned with a first translational axis of the machining device, and to slidably engage an arm fixture component of the arthroplasty jig blank.

16. The positioning component of claim 14, wherein the positioning component body comprises a second registration portion configured to be aligned with a second translational axis of the machining device, and to abut the arm fixture component when the first registration portion slidably engages the arm fixture component.

17. The positioning component of claim 14, wherein the positioning component body is configured to rotate about a first rotational axis of the machining device.

18. An arthroplasty jig blank comprising:
    a jig blank body; and
    an arm fixture component integral with the jig blank body, the arm fixture component comprising a U-shaped member extending from the jig blank body,
    wherein the arm fixture component is configured to be coupled to a machining device to position the jig blank body so that at least a portion of the jig blank body can be machined by the machining device and wherein the jig blank body includes at least one feature specific to a target anatomy site.

19. The arthroplasty jig blank of claim 18, wherein the jig blank body can be rotated about or translated along one or more axes of the machining device to allow machining of at least a portion of the jig blank body.

20. The arthroplasty jig blank of claim 18, wherein the arm fixture component is configured to be slidably coupled to a positioning component that is coupled to, or integral with, the machining device.

21. An arthroplasty jig manufacturing system comprising:
    first and second positioning components that are integral with, or configured to be coupled to, a computer numerical control machining device; and
    an arthroplasty jig blank comprising a jig blank body including at least one feature specific to a target anatomy site and an arm fixture component comprising at least one U-shaped member extending from the jig blank body,
    wherein the arm fixture component is configured to couple to the first positioning component and to the second positioning component, and wherein coupling the arm fixture component to the first and second positioning components positions the jig blank body for machining by the machining device.

* * * * *